US012714511B2

(12) United States Patent
Hendricks

(10) Patent No.: US 12,714,511 B2
(45) Date of Patent: Aug. 25, 2026

(54) SYSTEMS AND METHODS FOR A MULTIDIMENSIONAL TRACKING SYSTEM

(71) Applicant: Dignity Health, San Francisco, CA (US)

(72) Inventor: Benjamin Hendricks, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 412 days.

(21) Appl. No.: 18/551,639

(22) PCT Filed: Apr. 27, 2022

(86) PCT No.: PCT/US2022/026550
§ 371 (c)(1),
(2) Date: Sep. 21, 2023

(87) PCT Pub. No.: WO2022/232283
PCT Pub. Date: Nov. 3, 2022

(65) Prior Publication Data

US 2024/0164851 A1 May 23, 2024

Related U.S. Application Data

(60) Provisional application No. 63/285,624, filed on Dec. 3, 2021, provisional application No. 63/180,718, filed on Apr. 28, 2021.

(51) Int. Cl.
*A61B 34/20* (2016.01)
*A61B 90/00* (2016.01)
*A61B 90/20* (2016.01)

(52) U.S. Cl.
CPC .............. *A61B 34/20* (2016.02); *A61B 90/20* (2016.02); *A61B 90/37* (2016.02); *A61B 2034/2051* (2016.02)

(58) Field of Classification Search
None
See application file for complete search history.

(56) References Cited

U.S. PATENT DOCUMENTS

2008/0097195 A1 4/2008 Urquhart et al.
2014/0195988 A1* 7/2014 Kramer .................. G06F 3/017 715/863

(Continued)

FOREIGN PATENT DOCUMENTS

WO 202016355 A1 1/2020

OTHER PUBLICATIONS

Patent Cooperation Treaty, International Search Report and Written Opinion, International Application No. PCT/US2022/026550, date of mailing Aug. 2, 2022, 12 pages.

(Continued)

*Primary Examiner* — Helen Zong
(74) *Attorney, Agent, or Firm* — Polsinelli PC

(57) ABSTRACT

A multidimensional tracking system incorporates observed positions of objects tracked within various virtual spaces recorded by a plurality of hierarchical tracking systems based on observable positional relationships between the plurality of hierarchical tracking systems. In one embodiment, the multidimensional tracking system displays and records tracking and manipulation of physical objects over time relative to a virtual space. Further, the multidimensional tracking system can evaluate the accuracy of observed positions of objects as well as mappings that translate each virtual space to one another based on observable positional relationships between tracked objects.

46 Claims, 24 Drawing Sheets

(56) References Cited

U.S. PATENT DOCUMENTS

| | | | | |
|---|---|---|---|---|
| 2014/0240231 | A1 | 8/2014 | Minnen | |
| 2014/0325373 | A1 | 10/2014 | Kramer et al. | |
| 2015/0257718 | A1 * | 9/2015 | Iwamoto | A61N 5/1001<br>600/436 |
| 2016/0259329 | A1 | 9/2016 | High et al. | |
| 2017/0329413 | A1 | 11/2017 | Kramer et al. | |
| 2019/0038362 | A1 * | 2/2019 | Nash | A61B 90/36 |

OTHER PUBLICATIONS

European Patent Office, Extended European Search Report, Application No. 22796648.8, Feb. 18, 2025, 13 pages.

* cited by examiner

LOG 106

POSITIONS AND ORIENTATIONS (PER TIMESTAMP)

| OBJECT IDENTIFIER | OBSERVED | | | TRANSLATED | | | | | | EXPECTED | | |
|---|---|---|---|---|---|---|---|---|---|---|---|---|
| | $S_V$ | $S_{CHILD}$ | $S_{GC}$ | $S_{CHILD} \rightarrow S_V$ | $S_V \rightarrow S_{CHILD}$ | $S_{GC} \rightarrow S_{CHILD}$ | $S_{CHILD} \rightarrow S_{GC}$ | $S_{GC} \rightarrow S_V$ | $S_V \rightarrow S_{GC}$ | $S_V$ | $S_{CHILD}$ | $S_{GC}$ |
| TRACKING SUB-SYSTEMS | | | | | | | | | | | | |
| PARENT_TRACKING_SYSTEM ($S_V$) | (0,0,0) | (#,#,#) | N/A | (#,#,#) | (#,#,#) | (#,#,#) | (#,#,#) | (#,#,#) | (#,#,#) | (0,0,0) | (#,#,#) | (#,#,#) |
| ↳CHILD_TRACKING_SYSTEM ($S_{CHILD}$) | N/A | (0,0,0) | N/A | (#,#,#) | (#,#,#) | (#,#,#) | (#,#,#) | (#,#,#) | (#,#,#) | (#,#,#) | (0,0,0) | (#,#,#) |
| ↳GC_TRACKING_SYSTEM ($S_{GC}$) | N/A | (#,#,#) | (0,0,0) | (#,#,#) | (#,#,#) | (#,#,#) | (#,#,#) | (#,#,#) | (#,#,#) | (#,#,#) | (#,#,#) | (0,0,0) |
| TRACKED OBJECTS | | | | | | | | | | | | |
| OBJECT_1 | N/A | (#,#,#) | N/A | (#,#,#) | (#,#,#) | (#,#,#) | (#,#,#) | (#,#,#) | (#,#,#) | (#,#,#) | (#,#,#) | (#,#,#) |
| OBJECT_2 | N/A | (#,#,#) | (#,#,#) | (#,#,#) | (#,#,#) | (#,#,#) | (#,#,#) | (#,#,#) | (#,#,#) | (#,#,#) | (#,#,#) | (#,#,#) |
| LANDMARK OBJECTS | | | | | | | | | | | | |
| L_OBJECT_1 | N/A | N/A | (#,#,#) | (#,#,#) | (#,#,#) | (#,#,#) | (#,#,#) | (#,#,#) | (#,#,#) | (#,#,#) | (#,#,#) | (#,#,#) |
| L_OBJECT_2 | N/A | (#,#,#) | (#,#,#) | (#,#,#) | (#,#,#) | (#,#,#) | (#,#,#) | (#,#,#) | (#,#,#) | (#,#,#) | (#,#,#) | (#,#,#) |
| MARKER OBJECTS | | | | | | | | | | | | |
| MARKER_OBJECT_1 | (#,#,#) | (#,#,#) | (#,#,#) | (#,#,#) | (#,#,#) | (#,#,#) | (#,#,#) | (#,#,#) | (#,#,#) | (#,#,#) | (#,#,#) | (#,#,#) |
| MARKER_OBJECT_2 | (#,#,#) | (#,#,#) | (#,#,#) | (#,#,#) | (#,#,#) | (#,#,#) | (#,#,#) | (#,#,#) | (#,#,#) | (#,#,#) | (#,#,#) | (#,#,#) |

FIG. 1B

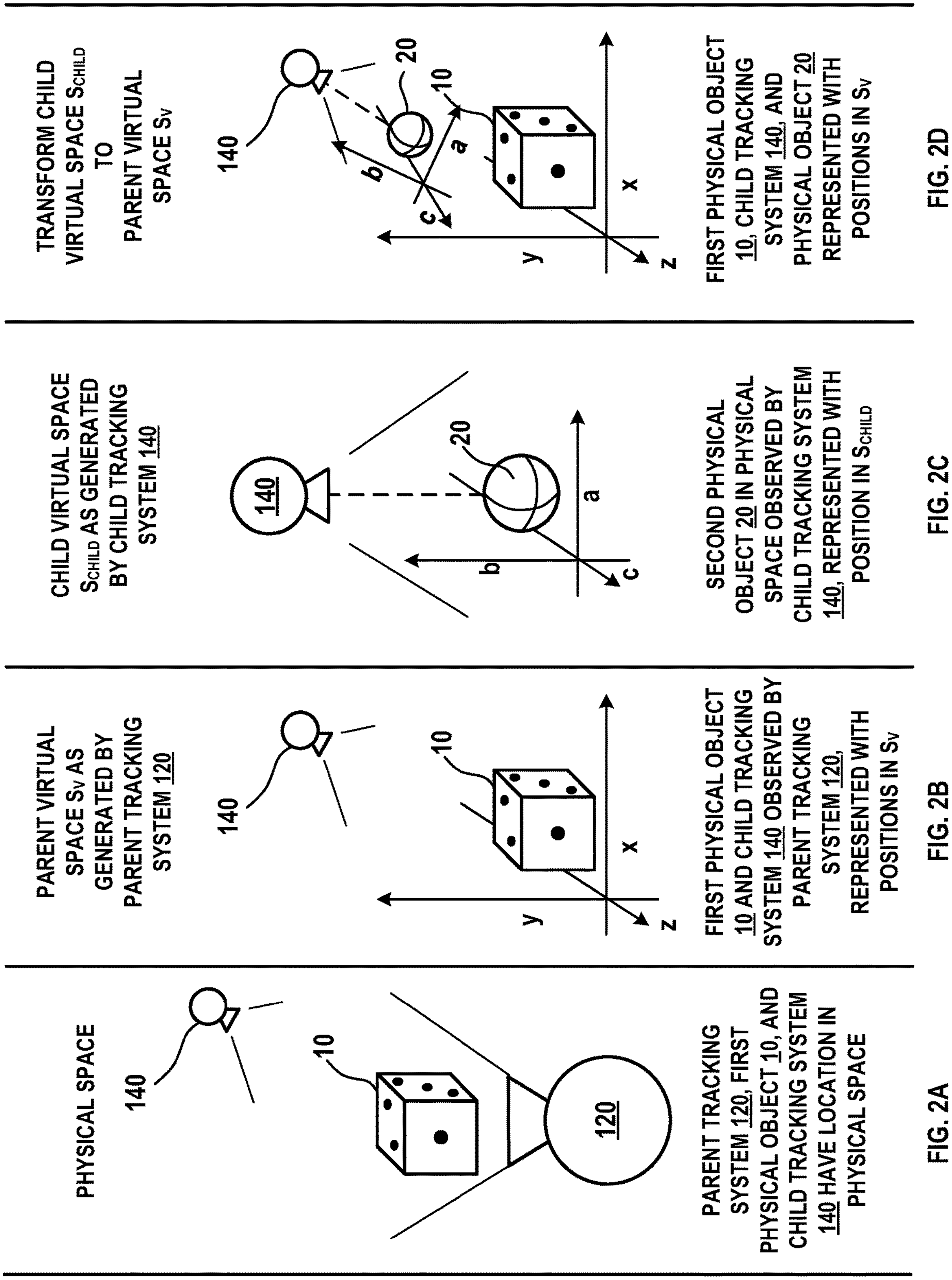

PHYSICAL SPACE
140
10
120
PARENT TRACKING SYSTEM 120, FIRST PHYSICAL OBJECT 10, AND CHILD TRACKING SYSTEM 140 HAVE LOCATION IN PHYSICAL SPACE
PARENT VIRTUAL SPACE S_V AS GENERATED BY PARENT TRACKING SYSTEM 120
140
10
y
x
z
FIRST PHYSICAL OBJECT 10 AND CHILD TRACKING SYSTEM 140 OBSERVED BY PARENT TRACKING SYSTEM 120, REPRESENTED WITH POSITIONS IN S_V
CHILD VIRTUAL SPACE S_CHILD AS GENERATED BY CHILD TRACKING SYSTEM 140
140
20
b
a
c
SECOND PHYSICAL OBJECT 20 IN PHYSICAL SPACE OBSERVED BY CHILD TRACKING SYSTEM 140, REPRESENTED WITH POSITION IN S_CHILD
TRANSFORM CHILD VIRTUAL SPACE S_CHILD TO PARENT VIRTUAL SPACE S_V
140
b
c
a
20
10
y
x
z
FIRST PHYSICAL OBJECT 10, CHILD TRACKING SYSTEM 140, AND PHYSICAL OBJECT 20 REPRESENTED WITH POSITIONS IN S_V

400

402 Record, by a parent tracking system, a first virtual space position representative of an observed physical position of a first tracked object in terms of a parent virtual space representative of the physical space, wherein the parent tracking system defines a parent tracking system position within the parent virtual space 404 Record, by a child tracking system, a second virtual space position representative of an observed physical position of the first tracked object in terms of a child virtual space representative of the physical space, wherein an observed physical position of the child tracking system is observed by the parent tracking system and defines a child tracking system position within the parent virtual space 406 Generate a first mapping between the child virtual space and the parent virtual space based on a first positional relationship between the parent tracking system position and the child tracking system position within the parent virtual space 408 Translate the second virtual space position of the first tracked object from the child virtual space to the parent virtual space based on a first mapping between the child virtual space and the parent virtual space.

410 Display, at a display device, a first image representative of the first tracked object in terms of the parent virtual space

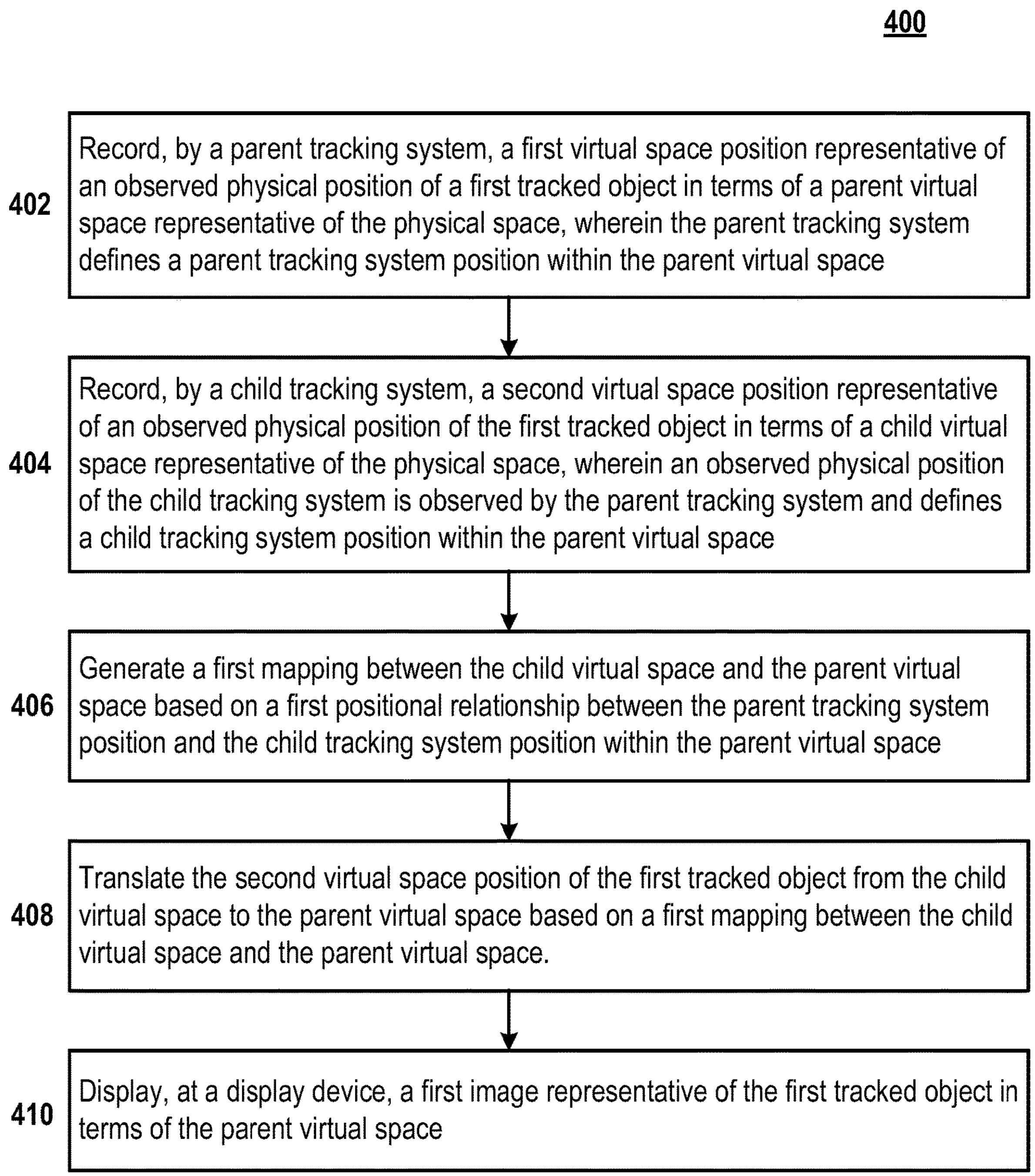

FIG. 15A 400 (cont'd)

402 Record, by a parent tracking system, a first virtual space position representative of an observed physical position of a first tracked object in terms of a parent virtual space representative of the physical space, wherein the parent tracking system defines a parent tracking system position within the parent virtual space 404 Record, by a child tracking system, a second virtual space position representative of an observed physical position of the first tracked object in terms of a child virtual space representative of the physical space, wherein an observed physical position of the child tracking system is observed by the parent tracking system and defines a child tracking system position within the parent virtual space 412 Record, by a grandchild tracking system, a third virtual space position representative of an observed physical position of the first tracked object in terms of a grandchild virtual space representative of the physical space, wherein an observed physical position of the grandchild tracking system is observable by the child tracking system and defines a grandchild tracking system position within the child virtual space 414 Generate a second mapping between the grandchild virtual space and the child virtual space based on a second positional relationship between the child tracking system position and the grandchild tracking system position within the child virtual space 416 Translate the third virtual space position of the first tracked object from the grandchild virtual space to the child virtual space based on the second mapping between the grandchild virtual space and the child virtual space 418 Translate the third virtual space position of the first tracked object from the child virtual space to the parent virtual space following translation of the third virtual space position from the grandchild virtual space to the child virtual space based on the first mapping between the child virtual space and the parent virtual space

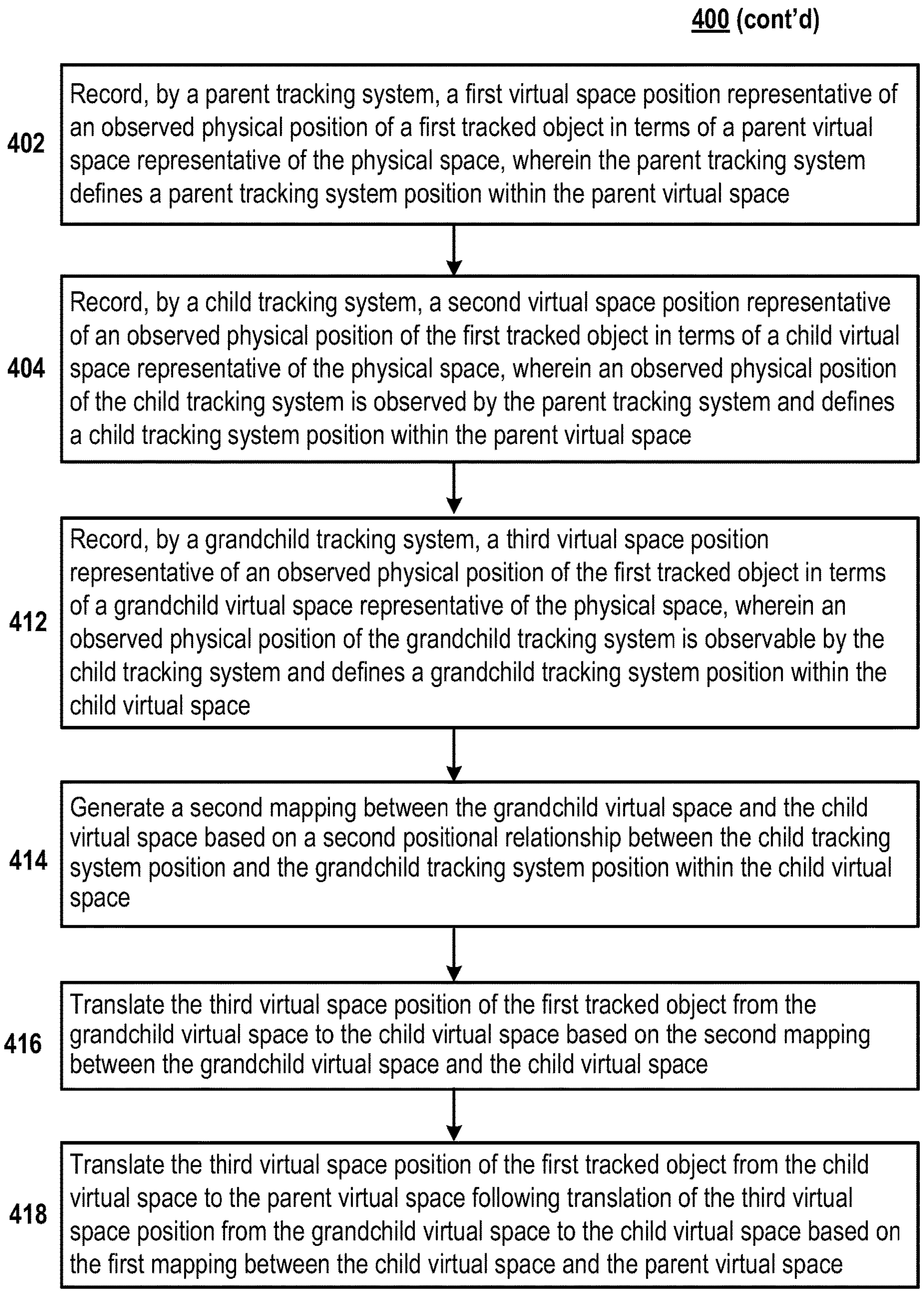

FIG. 15B 400 (cont'd)

402 Record, by a parent tracking system, a first virtual space position representative of an observed physical position of a first tracked object in terms of a parent virtual space representative of the physical space, wherein the parent tracking system defines a parent tracking system position within the parent virtual space 404 Record, by a child tracking system, a second virtual space position representative of an observed physical position of the first tracked object in terms of a child virtual space representative of the physical space, wherein an observed physical position of the child tracking system is observed by the parent tracking system and defines a child tracking system position within the parent virtual space 412 Record, by a grandchild tracking system, a third virtual space position representative of an observed physical position of the first tracked object in terms of a grandchild virtual space representative of the physical space, wherein an observed physical position of the grandchild tracking system is observable by the child tracking system and defines a grandchild tracking system position within the child virtual space 420 Record, by the child tracking system or the grandchild tracking system, a fourth virtual space position representative of an observed physical position of a second tracked object in terms of the child virtual space representative of the physical space or in terms of the grandchild virtual space representative of the physical space 422 Translate the fourth virtual space position of the second tracked object from the child virtual space or the grandchild virtual space to the parent virtual space based on the first mapping between the child virtual space and the parent virtual space or based on the second mapping between the grandchild virtual space and the child virtual space 424 Display, at the display device, a second image representative of a second tracked object in terms of the parent virtual space superimposed over the first image of the first tracked object

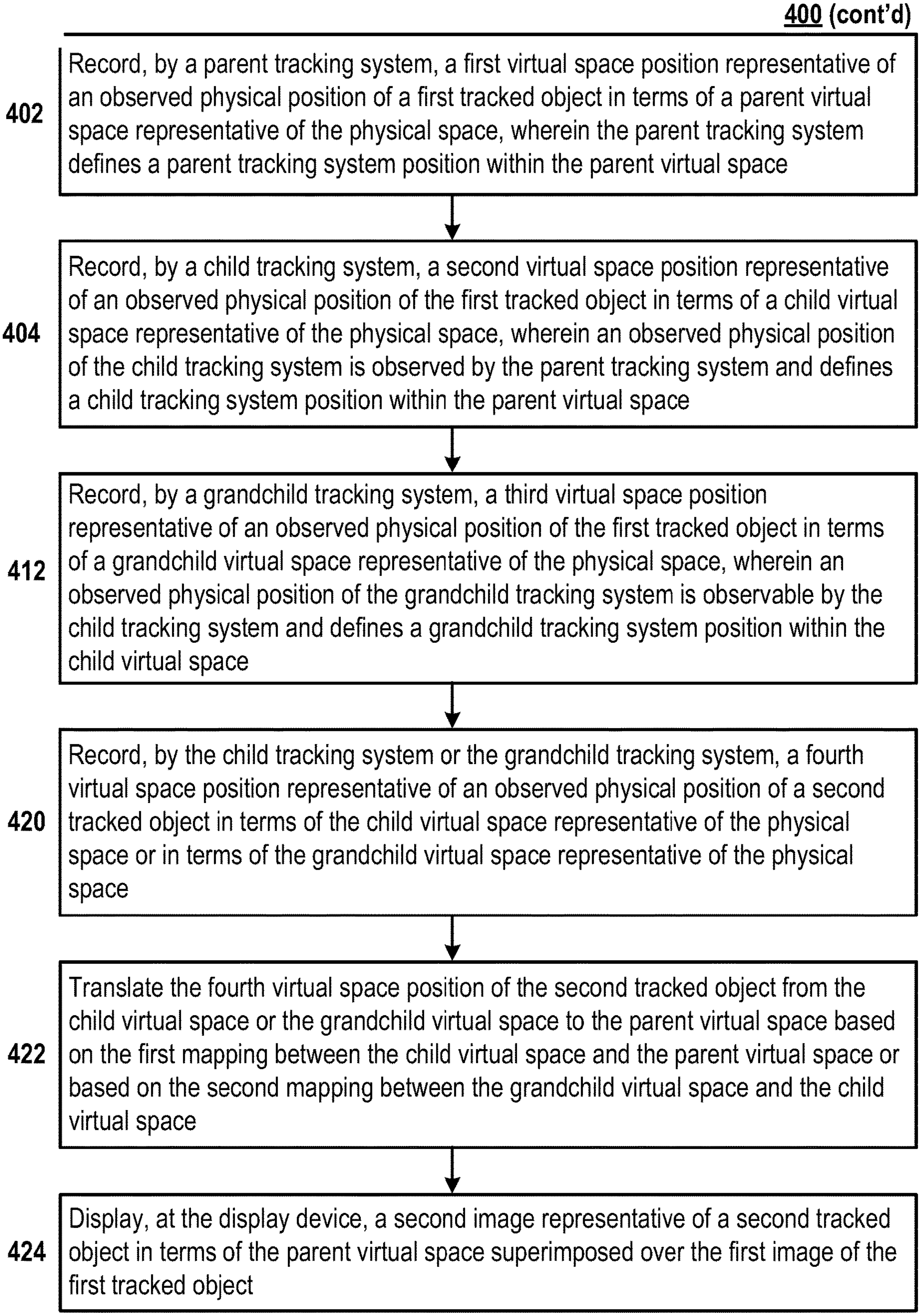

FIG. 15C 400 (cont'd)

430 Iteratively identify, for each tracked object of one or more tracked objects, a positional error between at least two of:

- the first virtual space position of the tracked object as represented within the parent virtual space;
- the second virtual space position of the tracked object as translated from the child virtual space to the parent virtual space; and/or
- the third virtual space position of the tracked object as translated from the grandchild virtual space to the parent virtual space 432 Update one or more positional estimation parameters of the grandchild tracking system, the child tracking system or the parent tracking system based on the positional error 434 Update the first mapping between the child virtual space and the parent virtual space or the second mapping between the grandchild virtual space and the child virtual space based on the positional error 436 Iteratively update a virtual space position of the associated tracked object within an object library based on a temporal difference between the first virtual space position, the second virtual space position, or the third virtual space position of the associated tracked object taken at a first timestamp and the first virtual space position, the second virtual space position, or the third virtual space position of the associated tracked object taken at a second timestamp

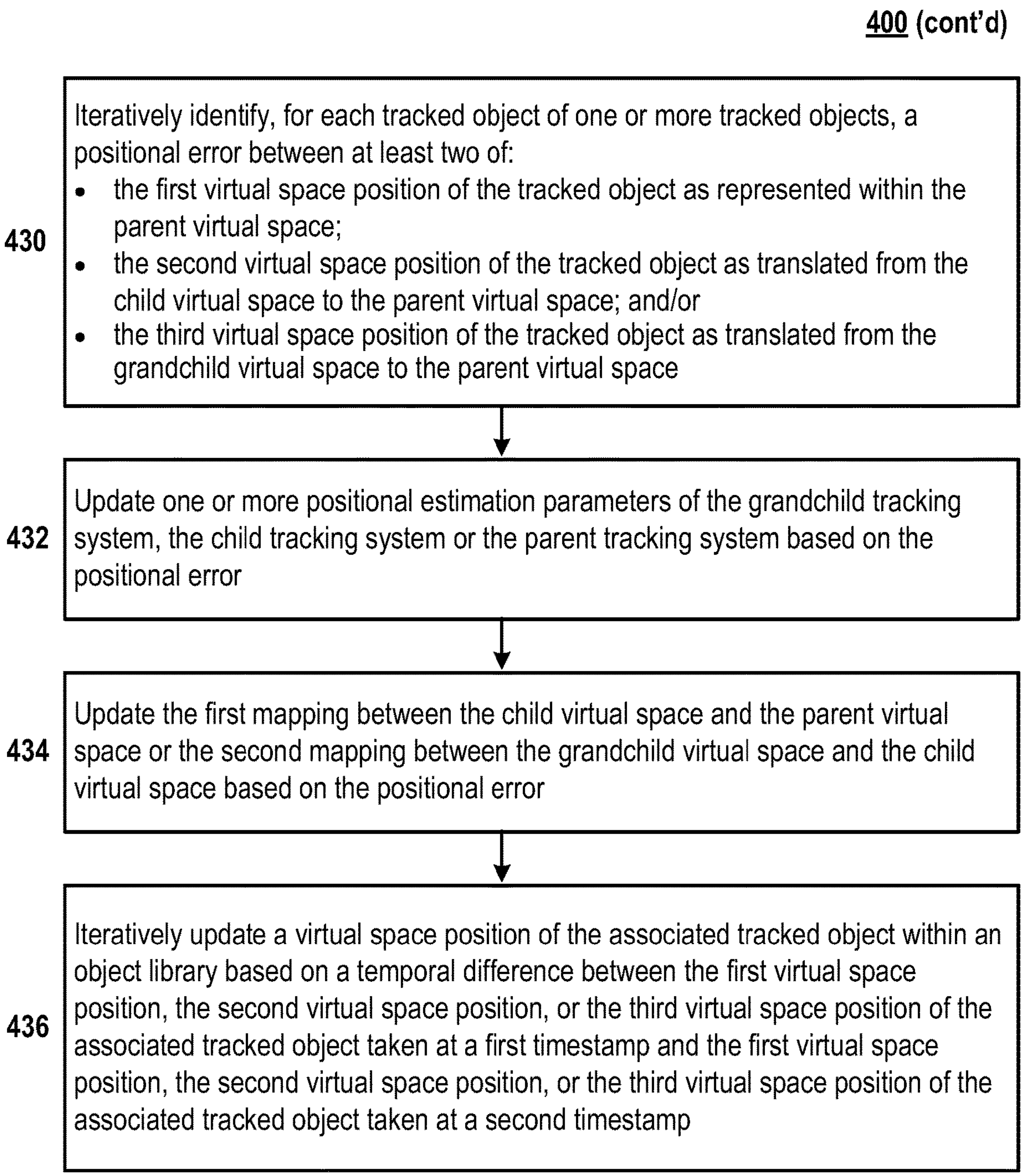

FIG. 15D 400 (cont'd)

440 Receive a fifth virtual space position indicative of an expected location of a landmark object relative to the parent virtual space, the child virtual space, and/or a grandchild virtual space 442 Display, at the display device, an identifier representative of the landmark object based on the fifth virtual space position of the landmark object with respect to the parent virtual space, the child virtual space, and/or the grandchild virtual space 444 Record, by the parent tracking system, the child tracking system or the grandchild tracking system, a sixth virtual space position representative of an observed physical position of the landmark object with respect to the parent virtual space, the child virtual space, and/or the grandchild virtual space 446 Iteratively identify a positional error between the fifth virtual space position of the landmark object and the sixth virtual space position of the landmark object with respect to the parent virtual space, the child virtual space or the grandchild virtual space 448 Update, at the display device, the identifier representative of the landmark object based on the sixth virtual space position of the landmark object with respect to the parent virtual space, the child virtual space, and/or the grandchild virtual space 450 Update one or more positional estimation parameters of the grandchild tracking system, the child tracking system and/or the parent tracking system based on the positional error

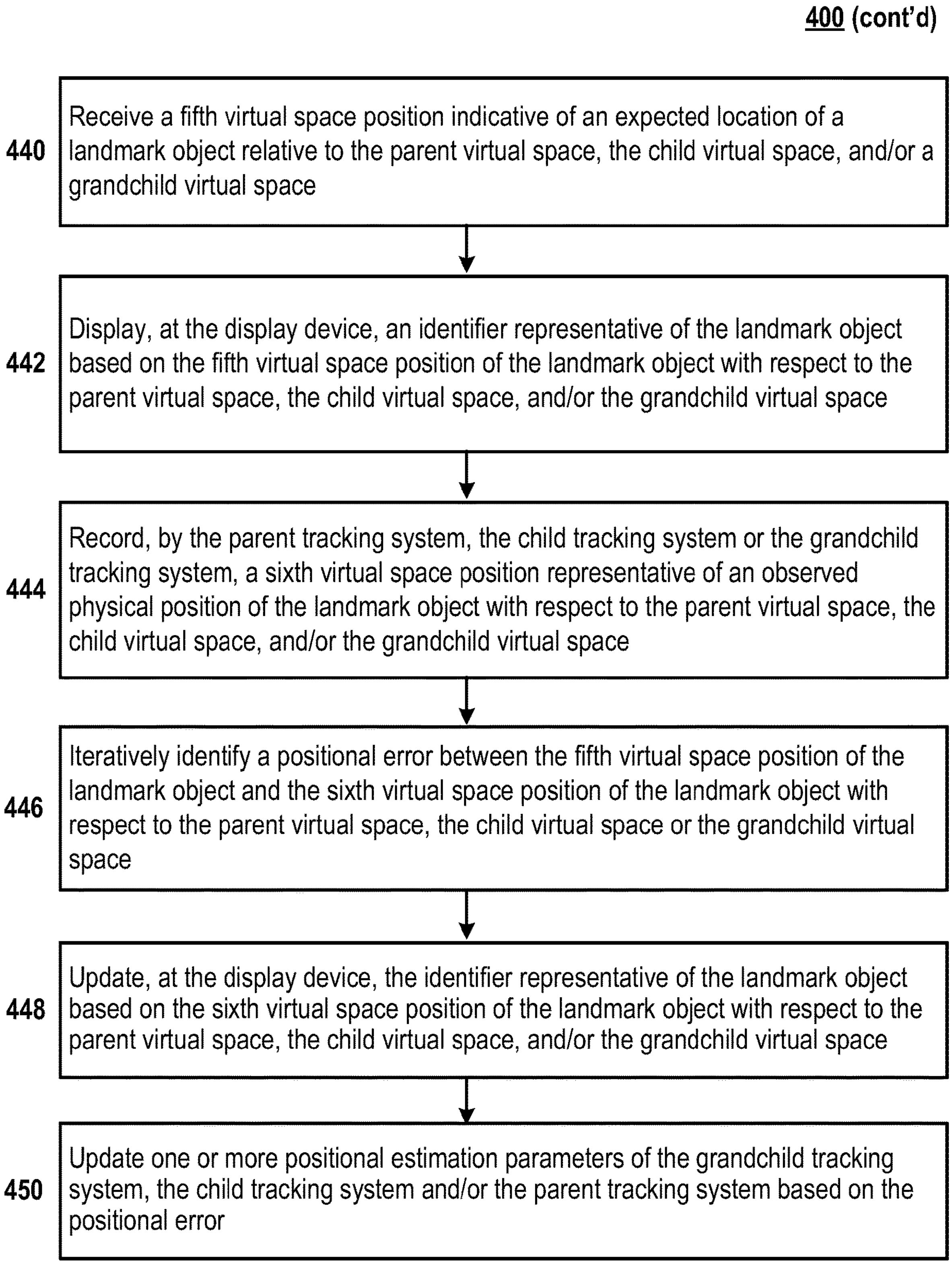

FIG. 15E

SYSTEMS AND METHODS FOR A MULTIDIMENSIONAL TRACKING SYSTEM

CROSS-REFERENCE TO RELATED APPLICATIONS

This is a PCT application that claims benefit to U.S. Provisional Patent Application Serial Nos. 63/180,718 filed 28 Apr. 2021 and 63/285,624 filed 3 Dec. 2021, which are herein incorporated by reference in its entirety.

FIELD

The present disclosure generally relates to tracking systems for surgical and non-surgical applications, and in particular, to a system and associated method for multi-modal position tracking of objects with respect to multiple interconnected tracking systems.

BACKGROUND

Both cranial and spinal surgical interventions possess bony landmarks that permit rigid fixation of optical trackers to allow digital representation of personalized anatomical features based on registration of an individual patient's cross-sectional imaging [ex. magnetic resonance imaging (MRI) or computed tomography (CT) scan]. Following registration of the optical or magnetic tracking sensor, an instrument with a 3-dimensional optical tracking frame can be manipulated relative to the individual patient's cranial or spinal anatomy, permitting this instrument to appear in digital Cartesian space and be represented relative to a digital display of the patient's anatomy. This technique formally referred to as stereotactic navigation, has permitted surgeons to conduct anatomically precise techniques for years within cranial and spinal surgeries.

The operating room microscope has been a staple for microsurgical procedures and therefore frame based stereotactic navigation has been adopted to implement this instrument as a trackable device in Cartesian space relative to the patient's anatomy. This permits the surgeon to know with reliable accuracy the focal point of the microscope within the digital space of the patient's cross-sectional imaging, in addition to the visualization of the focal point on the patient's actual anatomy.

However, while operating room microscopes and related microsurgical procedures have improved over time, current systems and devices may still suffer from limitations in accuracy, especially in terms of their ability to potentially track an object during a surgical procedure over an extended time period as positions of bodily landmarks and objects can drift over time. Many of these limitations in accurate tracking over an extended time can have the potential to cause fatal mistakes for a patient in a surgical procedure, for example.

It is with these observations in mind, among others, that various aspects of the present disclosure were conceived and developed.

BRIEF DESCRIPTION OF THE DRAWINGS

FIG. 1B is a simplified diagram showing an example log maintained by an object library of the system of FIG. 1A;

FIGS. 2A-2D are a series of simplified illustrations showing example virtual spaces defined by a parent tracking system and a child tracking system of the plurality of hierarchical tracking sub-systems;

FIGS. 15A-15E are a series of process flow charts showing an example method for multidimensional tracking according to the system of FIG. 1A;

Corresponding reference characters indicate corresponding elements among the view of the drawings. The headings used in the figures do not limit the scope of the claims.

DETAILED DESCRIPTION

Various embodiments of a multidimensional tracking system for various applications, including for microsurgical procedures, are disclosed herein. In particular, the multidimensional tracking system includes a "parent" tracking system in electrical communication with a computing system, the parent tracking system defining a "parent" virtual space representative of a physical space from the perspective of the parent tracking system. The parent tracking system is operable to record positions of a plurality of tracked objects relative to the parent virtual space. Further, the multidimensional tracking system includes a "child" tracking system in electrical communication with the computing system, the child tracking system defining a "child" virtual space representative of the physical space from the perspective of the child tracking system. The child tracking system is operable to record virtual space positions of a plurality of tracked objects relative to the child virtual space. In a preferred embodiment, the child tracking system is observed by the parent tracking system and defines a child tracking system position within the parent virtual space. The multidimensional tracking system relates the child virtual space to the parent virtual space through a first mapping based on a first positional relationship between the parent tracking system and the child tracking system. Using the first mapping, the multidimensional tracking system can translate positions of objects observed by the child tracking system to the parent virtual space for display and to show spatial relationships between objects tracked by the parent tracking system and the child tracking system. As will be discussed in further detail herein, the multidimensional tracking system can incorporate additional tracking systems including "grandchild" and "great-grandchild" tracking systems. Further, the multidimensional tracking system can provide multi-modal estimations of object positions by observing the same object with respect to a plurality of different spaces by a plurality of hierarchical tracking sub-systems and translating the observed positions across the plurality of different spaces, and across a temporal variable. This enables verification of accuracy, correction of one or more of the hierarchical tracking sub-systems, and correction of expected positions of objects, which can include anatomical structures when used in a surgical setting.

1. Multidimensional Tracking System Overview

Figure 1A:
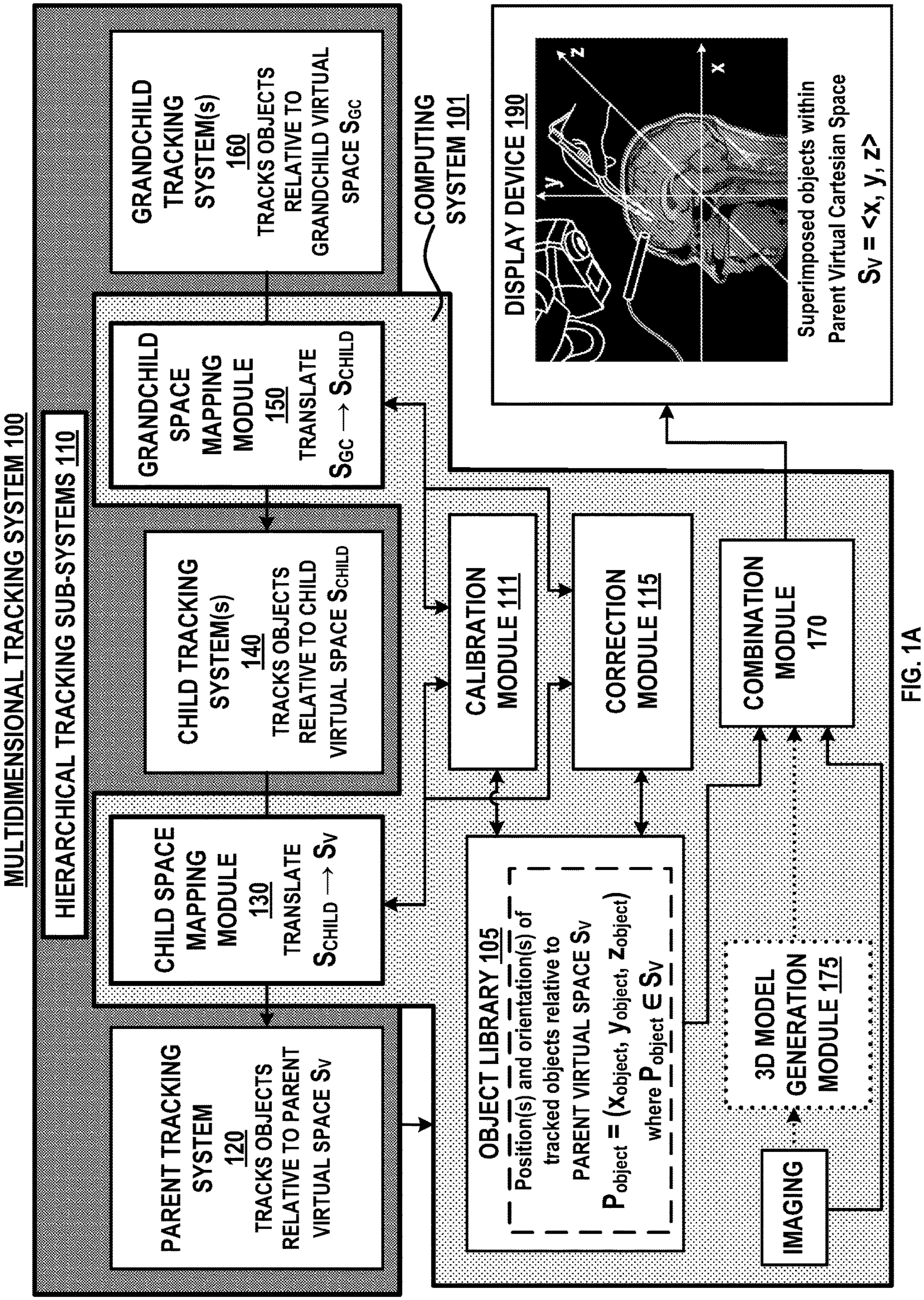
FIG. 1A is a simplified diagram showing a multidimensional tracking system for tracking one or more objects including a plurality of hierarchical tracking sub-systems in communication with a display device.

Referring to FIG. 1A, a multidimensional tracking system 100 includes a plurality of hierarchical tracking sub-systems 110 in communication with a computing system 101 that track a plurality of objects relative to a "parent" virtual space $S_V$ representative of a physical space. In particular, the plurality of hierarchical tracking sub-systems 110 includes a parent tracking system 120 that tracks physical positions and orientations of one or more objects relative to the parent virtual space $S_V$ from the perspective of the parent tracking system 120, and a child tracking system 140 that tracks physical positions and orientations of one or more objects relative to a child virtual space $S_{CHILD}$ from the perspective of the child tracking system 140. In some embodiments, the parent tracking system 120 is operable to track or otherwise observe a child tracking system position $P_{CHILD}$ of the child tracking system 140 with respect to the parent virtual space $S_V$, and the parent tracking system 120 also tracks or otherwise observes a parent tracking system position $P_{PARENT}$ of the parent tracking system 120 with respect to the parent virtual space $S_V$. As shown, the multidimensional tracking system 100 relates the child tracking system 140 to the parent tracking system 120 by a child space mapping module 130 that translates the child virtual space $S_{CHILD}$ to the parent virtual space $S_V$ based on a positional relationship between the child tracking system position $P_{CHILD}$ of the child tracking system 140 and the parent tracking system position $P_{PARENT}$ of the parent tracking system 120 and between orientations of the child tracking system 140 and the parent tracking system 120, enabling translation of positions of objects observed by the child tracking system 140 from the child virtual space $S_{CHILD}$ to the parent virtual space $S_V$. In some embodiments, the plurality of hierarchical tracking sub-systems 110 includes a plurality of child tracking systems 140 that each have individual relationships with the parent tracking system 120, and thus each have their own child mappings for translation of each respective child virtual space (e.g., $S_{CHILD\_1}$, $S_{CHILD\_2}$, . . . $S_{CHILD\_n}$) to the parent virtual space $S_V$.

Further, in some embodiments, the plurality of hierarchical tracking sub-systems 110 further includes a grandchild tracking system 160 that tracks physical positions and orientations of one or more objects relative to a grandchild virtual space $S_{GC}$ from the perspective of the grandchild tracking system 160. In some embodiments, the child tracking system 140 is operable to track or otherwise observe a grandchild tracking system position $P_{GC}$ of the grandchild tracking system 160 with respect to the child virtual space $S_{CHILD}$. As shown, the multidimensional tracking system 100 relates the grandchild tracking system 160 to the child tracking system 140 by a grandchild space mapping module 150 that translates the grandchild virtual space $S_{GC}$ to the child virtual space $S_{CHILD}$ based on a positional relationship between the grandchild tracking system position $P_{GC}$ of the grandchild tracking system 160 and the child tracking system position $P_{CHILD}$ of the child tracking system 140 and between orientations of the grandchild tracking system 160 and the child tracking system 140, enabling translation of positions of objects observed by the grandchild tracking system 160 from the grandchild virtual space $S_{GC}$ to the child virtual space $S_{CHILD}$. In some embodiments, the plurality of hierarchical tracking sub-systems 110 includes a plurality of grandchild tracking systems 160 that each have individual relationships with a respective child tracking system 140, and thus each have their own mappings for translation of each respective grandchild virtual space (e.g., $S_{GC\_1}$, $S_{GC\_2}$ . . . . $S_{GC\_m}$) to an associated child virtual space (e.g., $S_{CHILD\_1}$, $S_{CHILD\_2}$ . . . . $S_{CHILD\_n}$), which can each in turn be mapped to the parent virtual space $S_V$. It should be noted that the plurality of hierarchical tracking sub-systems 110 can further include one or more great-grandchild tracking systems (such as great-grandchild tracking system 380 shown in a later example of FIG. 13) or one or more great-great-grandchild tracking systems, etc. For the sake of brevity, this disclosure will include discussion of the grandchild tracking system 160, and hypothetical "great-grandchild" tracking systems, "great-great-grandchild" tracking systems, and the like can be inherently treated as "child" or "grandchild" tracking systems of the grandchild tracking system 160.

As readily apparent to one of skill in the art, embodiments of the multidimensional tracking system 100 may be used in multiple commercial applications and systems and is in no way intended to be limited to only use in conjunction with surgical or microsurgical procedures. The multidimensional tracking system 100 can provide various advantages that may be achieved as well as incorporated in other processes, including and not limited to: multiple educations, analytical, efficiency, quality improvement, and outcome-altering applications within a surgical realm.

1.1 Object Library and Error Correction Overview

As further shown in FIG. 1A, the multidimensional tracking system 100 can maintain or otherwise include an object library 105 that receives and stores data indicative of positions and orientations of a plurality of tracked objects relative to the parent virtual space $S_V$, including observed positions, translated positions and/or expected positions of each tracked object of the plurality of tracked objects in the parent, child, and/or grandchild virtual spaces $S_V$, $S_{CHILD}$ or $S_{GC}$. As the plurality of hierarchical tracking sub-systems 110 update observed positions of each tracked object over time, the multidimensional tracking system 100 updates the object library 105 to include the updated observed positions and translates the observed positions to one or more parent, child, or grandchild virtual spaces $S_V$, $S_{CHILD}$ or Sec, enabling the multidimensional tracking system 100 to identify and correct errors and maintain a reliable log of object positions over time. In some embodiments, with additional reference to FIG. 1B, such as for surgical applications, a log 106 maintained by the object library 105 can be used to analyze surgical cases and approaches; the log 106 can be used for examining the effects of surgical approach on anatomy (such as shifting of anatomical structures during surgery) and can also be used for identifying mistakes or for recording "master" cases that demonstrate correct technique. In the example shown, the log 106 can include observed positions, translated positions, and/or expected positions of objects for a plurality of timestamps including each respective hierarchical tracking sub-system 110, tracked objects, landmark objects, and marker objects. The example shows observed, expected or translated positional values listed generically as "(#, #, #)", and further shows "N/A" for values that are not available. For example, tracked object Object_1 might not be directly observed by parent tracking system 120, as a result there would be no observed position for tracked object Object_1 in the parent virtual space $S_V$, but if tracked object Object_1 is observed by the child tracking system 140, then the observed position can also be translated from the child virtual space $S_{CHILD}$ to the parent virtual space $S_V$. Expected positions for each respective hierarchical tracking sub-system 110 can be at the origin (0,0,0) of their respective virtual spaces, although it should be noted that not all embodiments of the multidimensional tracking system 100 might require this condition. Translated position redundancies can be used to verify mappings and/or observed positions, as will be discussed in greater detail herein with respect to a correction module 115. As will also be discussed in greater detail, the multidimensional tracking system 100 can incorporate one or more previously recorded logs 106 as "master cases" by master surgeons into a workflow by displaying relevant information at the display device 190 at certain locations within the surgical space, including directions towards one or more landmark objects.

As shown and as will be discussed in greater detail herein, the multidimensional tracking system 100 can include a calibration module 111 that enables calibration of various parameters of the multidimensional tracking system 100 for correct positional estimation and mapping generation. The multidimensional tracking system 100 further includes the correction module 115 in communication with the object library 105 that updates various parameters of the multidimensional tracking system 100 based on errors and discrepancies between translated positions, expected positions, and actual observed positions of tracked objects. As such, the multidimensional tracking system 100 continually corrects erroneous observed positions and expected positions of tracked objects by continually evaluating the accuracy of observed positions recorded by each respective hierarchical tracking sub-system 110.

Since the positions of each respective hierarchical tracking sub-system 110 including the parent tracking system 120, the child tracking system(s) 140 and grandchild tracking system(s) 160 can change over time, the multidimensional tracking system 100 can iteratively update the mappings between each respective hierarchical tracking sub-system 110 based on observable positional relationships, including positions and orientations, between each respective hierarchical tracking sub-system 110 and objects, including marker objects and landmark objects, tracked by each respective hierarchical tracking sub-system 110. As such, the multidimensional tracking system 100 continually corrects mapping errors and inconsistencies to ensure correct translation between spaces.

As further shown in FIG. 1A, the multidimensional tracking system 100 includes a combination module 170 that combines the information maintained within the object library 105 with imaging representative of the physical space and displays the information at a display device 190. In some embodiments, the multidimensional tracking system 100 displays one or more images indicative of one or more tracked objects superimposed over one another within the parent virtual space $S_V$. Optionally, the multidimensional tracking system 100 can include a 3D model generation module 175 that forms a 3D model from a plurality of cross-sectional images that are used to represent an object within the parent virtual space $S_V$, which will be discussed in a later section of the present disclosure. In some embodiments, the multidimensional tracking system 100 can incorporate recollection of one or more "master" cases through virtual projection of an object including potential manipulation of the object to a display device 190, which can include augmented reality display within microscope or other tracking system oculars, projected in physical space, or within a VR environment.

1.2 Virtual Spaces Example

FIGS. 2A-2D provide a simplified illustration of the virtual spaces as described above. In particular, FIG. 2A shows an example physical space including a parent tracking system 120 that observes a first physical object 10 and a child tracking system 140, with all three having their own physical positions in the physical space. It should be noted that the parent tracking system 120, the child tracking system 140, and the first physical object 10 are all considered to be objects within the physical space. FIG. 2B shows an example parent virtual space $S_V=\langle x,y,z \rangle$ as generated by the parent tracking system 120, with the first physical object 10 defining a position $P_{first\_object}=(x_{first}, y_{first}, z_{first})$ in the parent virtual space $S_V$ and with the child tracking system 140 defining a position $P_{child}=(x_{child}, y_{child}, z_{child})$ in the parent virtual space $S_V$. FIG. 2C shows an example child virtual space $S_{CHILD}=\langle a,b,c \rangle$ as generated by the child tracking system 140, where the child tracking system 140 observes a second physical object 20 that may or may not be observed by the parent tracking system 120. The second physical object 20 defines a position $P_{second_object}=(a_{second}, b_{second}, C_{second})$ in the child virtual space $S_{CHILD}$. FIG. 2D shows an example transformation of the child virtual space $S_{CHILD}$ to the parent virtual space $S_V$, where the second physical object 20 is represented within the parent virtual space $S_V$ along with the first physical object 10 and the child tracking system 140. The second physical object 20 can be represented within the parent virtual space $S_V$ as $P_{second\_object}'=(x_{second}', y_{second}', z_{second}')$ through translation according to a mapping between the child virtual space $S_{CHILD}$ and the parent virtual space $S_V$, which is based on the positional relationships (including position and orientation) between the child tracking system 140 having tracking system position $P_{child}=(x_{child}, y_{child}, z_{child}) \in S_V$ and the parent tracking system 120 that defines the parent virtual space $S_V$.

In the example shown, the parent tracking system 120 observes the positions and orientations of the child tracking system 140 and the first physical object 10 as long as the child tracking system 140 and the first physical object 10 are within a line-of-sight of the parent tracking system 120, however it should be noted that in other embodiments, the hierarchical tracking sub-systems 110 are not limited to this. In particular, the hierarchical tracking sub-systems 110 can track positions and orientations of objects and/or themselves by various methods including optical, mechanical, electromagnetic, sonic (e.g., ultrasound for surgical applications and/or sonar for non-surgical applications), and computer-vision techniques. The inclusion of more than one type of tracking method that can be employed by the hierarchical tracking sub-systems 110 enables the multidimensional tracking system 100 to estimate positions and orientations of objects and the hierarchical tracking sub-systems 110 in a multimodal manner.

1.3 Object Position Tracking and Calibration

Object position tracking has historically been attempted through various methods, such as mechanical, electromagnetic, sonic (e.g., ultrasound or sonar), computer-vision techniques, and optical methods. Further, some current day operative microscopes have adopted the use of binocular or stereo-camera visualization technology which permits applications such as 3-dimensional video recording. Orientation tracking has also been historically attempted through means such as inertial measurement units (IMUs). In accordance with various embodiments herein, each respective hierarchical tracking sub-system 110 can employ object position tracking and orientation tracking through the aforementioned methods and/or binocular or stereo-camera visualization technology. Various examples of optical tracking by at least one hierarchical tracking sub-system 110 are provided throughout. In the optical example of FIG. 3A, the parent tracking system 120 observes the child tracking system 140 and the grandchild tracking system 160 within its “field-of-view”; the child tracking system 140 observes the grandchild tracking system 160 within its “field-of-view”; and the grandchild tracking system 160 observes the parent tracking system 120 and the child tracking system 140 within its “field-of-view”. However, it should be noted that “field-of-view” tracking is not always feasible or straightforward, especially when trying to relate hierarchical tracking sub-systems 110 to one another. As such, the hierarchical tracking sub-systems 110 can also use additional tracking methods. In some embodiments, one or more of the hierarchical tracking sub-systems 110 can implement one or more machine learning models (not shown) for object tracking and positional estimation.

Figure 3A:
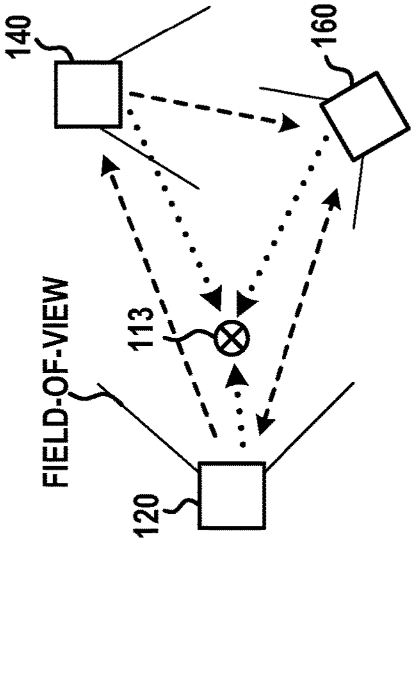
FIGS. 3A-3C are a series of simplified illustrations showing various object detection methodologies that can be employed by the plurality of hierarchical tracking sub-systems of FIG. 1A, which can be aided by one or more marker objects.
Figure 3B:
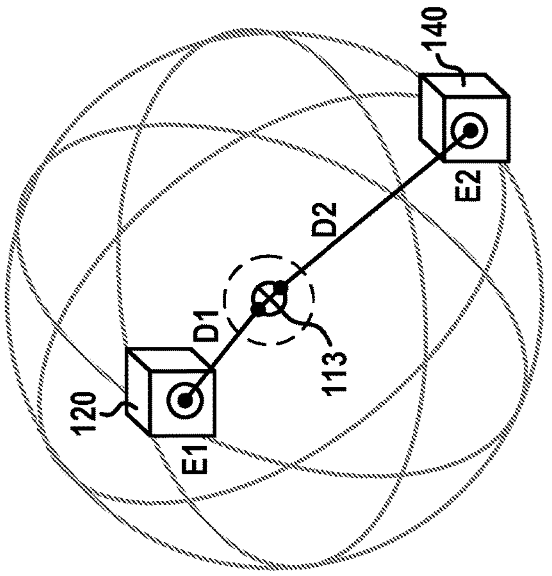
Figure 3C:
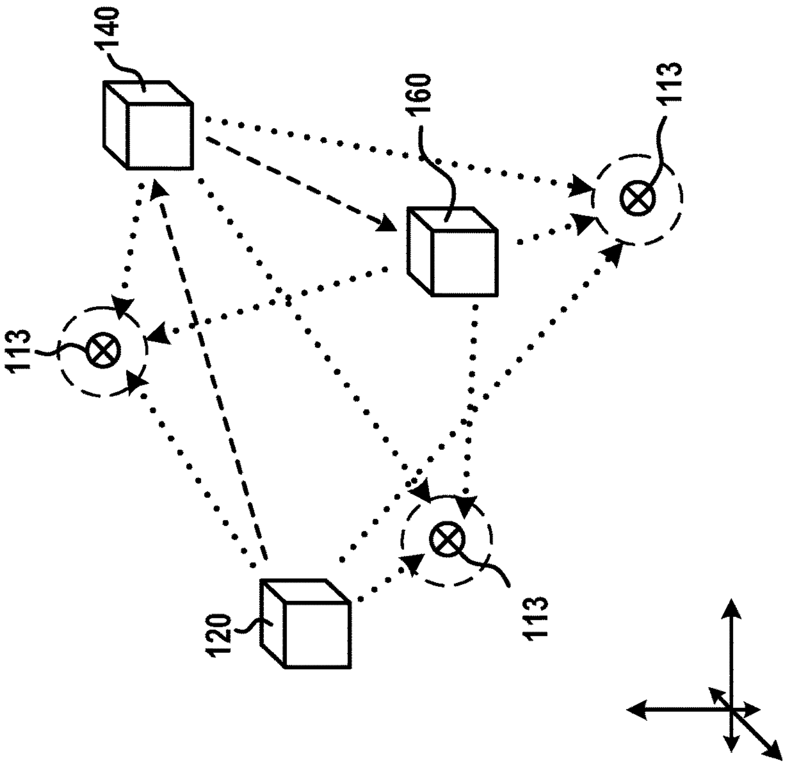

In some embodiments, the multidimensional tracking system 100 can include one or more marker objects 113 that can be placed at fixed positions in the physical space to act as universal reference points that the multidimensional tracking system 100 can calibrate itself to and use to check its accuracy. The one or more marker objects 113 can be suited for tracking by the plurality of hierarchical tracking sub-systems 110 through optical methods, sonic methods (e.g., ultrasound for surgical applications or sonar for non-surgical applications), electromagnetic methods, or combinations thereof. An example of optical-based tracking of a marker object 113 is shown in FIG. 3A, and an example of electromagnetic-based tracking is shown in FIG. 3B. For electromagnetic-based tracking, at least one hierarchical tracking sub-system 110 can observe a strength of an electromagnetic field generated by an object to be tracked, which can include another hierarchical tracking sub-system 110 or a marker object 113 that can be placed at a fixed position within the physical space. In the example of FIG. 3B, the parent tracking system 120 and the child tracking system 140 both observe the marker object 113 not through direct optical observation but by measuring one or more parameters indicative of an electromagnetic field strength (e.g., E1 and E2), which can be correlated with a distance (e.g., D1 and D2) from the marker object 113. As shown in the example of FIG. 3C, a plurality of marker objects 113 placed throughout the physical space and universally observable by the parent tracking system 120, the child tracking system 140 and/or the grandchild tracking system 160 can aid the multidimensional tracking system 100 in calibrating itself and maintaining accurate readings of observed objects and mappings between the plurality of hierarchical tracking sub-systems 110.

Fiducial markers (such as marker objects 113) have been historically used as a universal reference for stereotactic navigation systems. In some embodiments, the marker objects 113 can be a radiopaque or MRI-visible structure that are affixed to a patient’s scalp and provide a reference point for registration of a virtual space during imaging (e.g., MRI imaging) and relation of the virtual space to the physical space because fiducial markers can be visible in both environments. Stereotactic navigation systems have also adopted the ability to isolate the outside of the patient’s skin on the virtual space and watch as a probe draws out this space in the operating room, in which the stereotactic navigation system defines one or more first points of occupied space in the virtual space (corresponding with skin as visible within imaging) by dragging a probe being watched by the optical tracker along the patient’s scalp. Importantly, usually a minimum of 3 and more likely 4 reference points in physical/virtual space are needed for calibration. The multidimensional tracking system 100 can be calibrated in more than one way:

(1) A practitioner can instruct the multidimensional tracking system 100 to define one or more points in the physical space and a virtual space that serve as reference points for all the tracking systems. This can include registering one or more landmark objects including anatomical landmarks such as certain bony landmarks, arteries, or positions along a cortex (in the case of cranial surgery). Alternatively, landmark objects can also include implants or marker objects placed within the surgical field that maps to all virtual spaces and is readily detectible.

(2) The multidimensional tracking system 100 analyzes a virtual space and defines one or more landmark regions for reference (for example, registering one or more positional points taken along the skin with a probe as landmark objects).

Figure 3D:
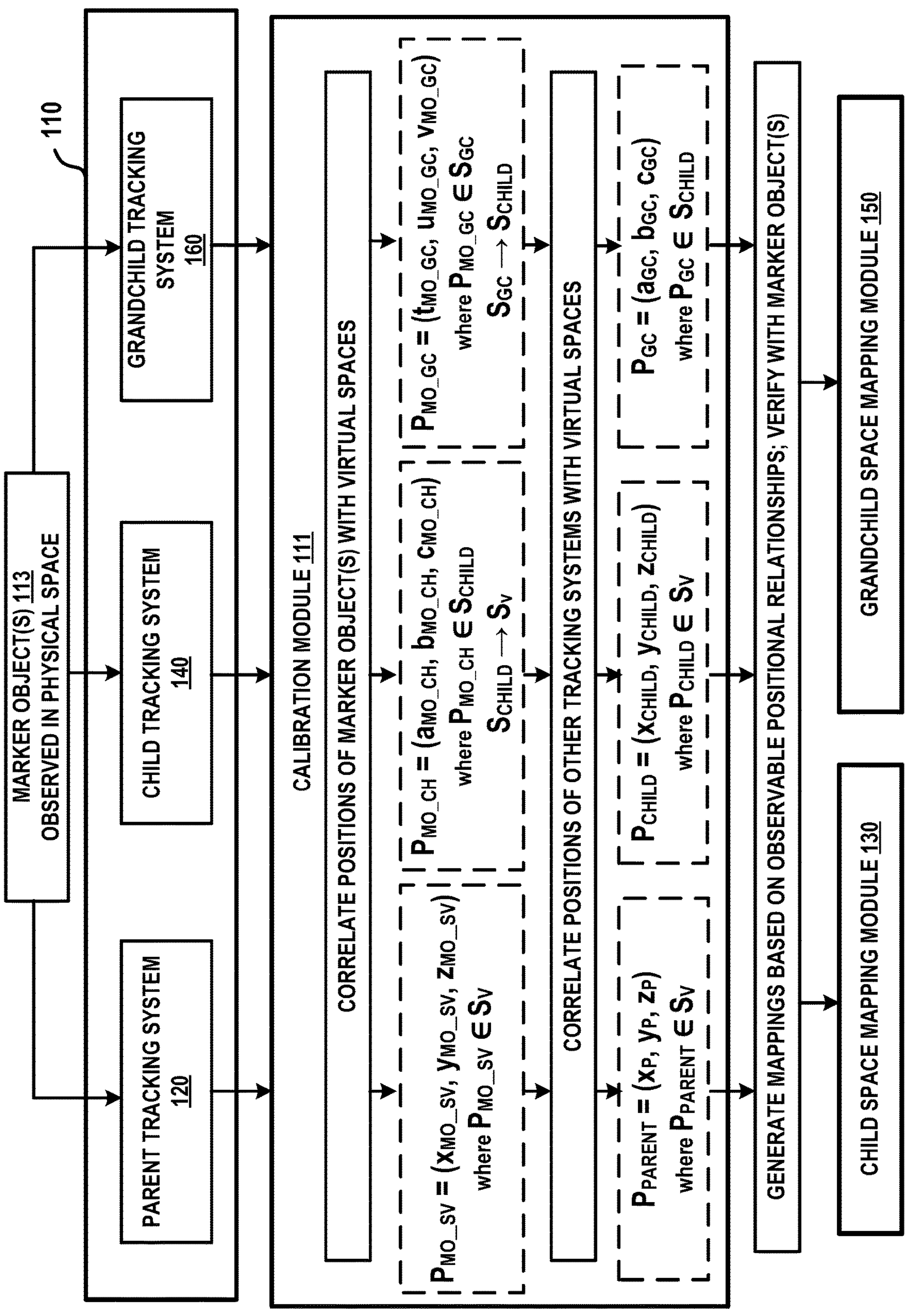
FIG. 3D is a simplified diagram showing a calibration module for calibration of the system of FIG. 1A.

Referring briefly to FIG. 3D, the multidimensional tracking system 100 can calibrate itself by the calibration module 111 in communication with the hierarchical tracking sub-systems 110. As shown, in some embodiments, the plurality of hierarchical tracking sub-systems 110 can each observe physical positions of objects including marker objects 113 and/or landmark objects in the physical space, and each hierarchical tracking sub-system 110 defines a respective virtual space. In some embodiments, the calibration module 111 correlates positions of marker objects 113 to each virtual space. In the example, the parent tracking system 120 observes a position of a marker object 113 as $P_{MO\_SV}=(x_{MO\_SV}, y_{MO\_SV}, z_{MO\_SV})$ where $P_{MO\_SV} \in S_V$, the child tracking system 140 observes a position of the marker object 113 as $P_{MO\_CH}=(a_{MO\_CH}, b_{MO\_CH}, C_{MO\_CH})$ where $P_{MO\_CH}$ E $S_{CHILD}$, and the grandchild tracking system 160 observes a position of the marker object 113 as $P_{MO\_GC}=(t_{MO\_GC}, u_{MO\_GC}, v_{MO\_GC})$ where $P_{MO\_CH}$ E $S_{GC}$. The calibration module 111 also correlates positions and orientations of the plurality of hierarchical tracking sub-systems 110 to each virtual space (e.g., parent tracking system position $P_{PARENT}=(x_P, y_P, z_P)$ where $P_{PARENT}$ E $S_V$; child tracking system position $P_{CHILD}=(x_{CHILD}, y_{CHILD}, z_{CHILD})$ where $P_{CHILD} \in S_V$; grandchild tracking system position $P_{GC}=(a_{GC}, b_{GC}, c_{GC})$ where $P_{GC} \in S_{CHILD}$). With these spatial relationships defined with respect to the virtual spaces, the multidimensional tracking system 100 can generate the mappings between each respective hierarchical tracking sub-system 110 based on observable positional relationships, including positions and orientations, between each respective hierarchical tracking sub-system 110 and objects tracked by each respective hierarchical tracking sub-system 110. This mapping generation step can be handled by child space mapping module 130 and grandchild space mapping module 150 and can be verified against the observed positions of the marker objects 113 by correction module 115.

2. Example Surgical Application

Figure 4A:
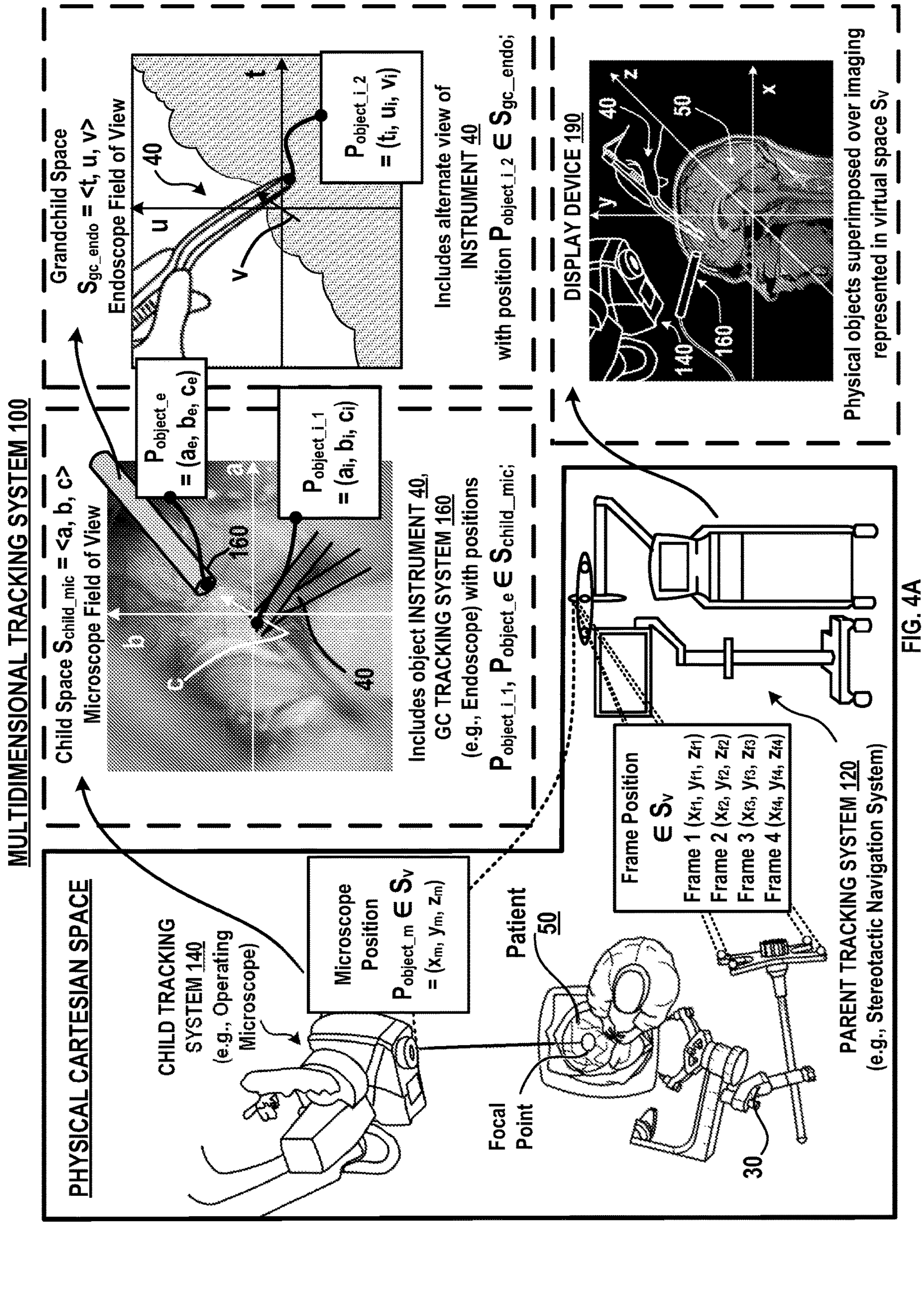
FIG. 4A is a diagram showing an example multidimensional tracking system according to the diagram of FIG. 1A in a surgical setting.

FIG. 4A illustrates an example surgical application of the multidimensional tracking system 100 that includes a stereotactic navigation system (SNS) as a parent tracking system 120, an operating microscope (OM) as a child tracking system 140, and an endoscope as a grandchild tracking system 160. The parent tracking system 120 observes a patient in the physical space as a patient object 50 within the parent virtual space $S_V$, whose imaging is displayed in terms of the parent virtual space $S_V=\langle x, y, z\rangle$ on a display device 190. In the example shown, the parent tracking system 120 observes a position of the patient object 50 by receiving positions of one or more points on a stereotactic frame 30 that is fixed in the physical space relative to the patient object 50 that are represented in the parent virtual space $S_V$ to relate the physical position and orientation of the patient object 50 in the physical space to the parent virtual space $S_V$ (e.g., Frame observed positions $\in S_V$; Frame 1 $(x_{f1}, y_{f1}, z_{f1}) \in S_V$; Frame 2 $(x_{f2}, y_{f2}, z_{f2}) \in S_V$; Frame 3 $(x_{f3}, y_{f3}, z_{f3}) \in S_V$; Frame 4 $(x_{f4}, y_{f4}, z_{f4}) \in S_V$). In some embodiments, the position of the parent tracking system 120 can also remain fixed in the physical space relative to the patient object 50 and stereotactic frame 30. The parent tracking system 120 can also observe a physical position of the child tracking system 140 in terms of the parent virtual space $S_V$ (e.g., OM observed position $P_{object\_m} \in S_V=(x_m, y_m, z_m)$).

As shown, the child tracking system 140 defines a child virtual space $S_{child\_mic}=\langle a, b, c\rangle$. FIG. 4A shows an example field-of-view of the child tracking system 140, which includes an instrument object 40 and the grandchild tracking system 160, which can be an endoscope in this example. As shown, the instrument object 40 defines an observed first position $P_{object\_i\_1}$ within the child virtual space $S_{child\_mic}$ (e.g., $P_{object\_i\_1}=(a_i, b_i, c_i) \in S_{child\_mic}$), and the grandchild tracking system 160 defines an observed position $P_{object\_e}$ within the child virtual space $S_{child\_mic}$ (e.g., $P_{object\_e}=(ae, be, Ce) \in S_{child\_mic}$). The observed first position $P_{object\_i\_1}$ E $S_{child\_mic}$ of the instrument object 40 and the observed position $P_{object\_e} \in S_{child\_mic}$ of the grandchild tracking system 160 can be translated from the child virtual space $S_{child\_mic}$ to the parent virtual space $S_V$ based on the positional relationship between the parent tracking system 120 (SNS) and the child tracking system 140 (OM). Note that the instrument object 40 might not track its own position; and that the grandchild tracking system 160 is also considered an object that can be tracked by the child tracking system 140 (OM) and/or the parent tracking system 120 (SNS). Further, in some embodiments, the stereotactic frame 30 can represent a surrogate for the patient object 50 given the fixed association with the patient object 50 as observed by the parent tracking system 120 (SNS).

The grandchild tracking system 160 (endoscope) defines a grandchild virtual space $S_{gc\_endo}=\langle t, u, v\rangle$. FIG. 4A shows an example field-of-view of the grandchild tracking system 160, which includes an alternate view of the instrument object 40 having an observed second position $P_{object\_i\_2}$ within the grandchild virtual space $S_{gc\_endo}$ (e.g., $P_{object\_i\_2}=(t_i, u_i, v_i) \in S_{gc\_endo}$). The multidimensional tracking system 100 can translate the observed second position $P_{object\_i\_2} \in S_{gc\_endo}$ of the instrument object 40 from the grandchild virtual space $S_{gc\_endo}$ to the child virtual space $S_{child\_mic}$ to obtain a second translated position $P_{object\_i\_2}' \in S_{child\_mic}$ based on the positional relationship between the grandchild tracking system 160 (endoscope) and the child tracking system 140 (OM), and can further translate the second translated position $P_{object\_i\_2}' \in S_{child\_mic}$ from the child virtual space $S_{child\_mic}$ to the parent virtual space $S_V$ to obtain a second twice-translated position $P_{object\_i\_2}'' \in S_V$ based on the positional relationship between the parent tracking system 120 (SNS) and the child tracking system 140 (OM).

As shown, the multidimensional tracking system 100 represents positions of tracked objects including the patient object 50, child tracking system 140 (OM), instrument object 40, and the grandchild tracking system 160 by superimposing images of each at their respective positions within the parent virtual space $S_V$ at the display device 190 following translation and accuracy verification of each position to the parent virtual space $S_V$. Optionally, the multidimensional tracking system 100 can also represent positions of tracked objects within any other virtual space including the child virtual space $S_{child\_mic}$ or the grandchild virtual space $S_{gc\_endo}$ at the display device 190 following translation and accuracy verification of each position to the child virtual space $S_{child\_mic}$ or the grandchild virtual space $S_{gc\_endo}$.

For this example, since the instrument object 40 has two positional readings in two different virtual spaces (grandchild virtual space $S_{gc\_endo}$ and child virtual space $S_{child\_mic}$), the multidimensional tracking system 100 can verify the estimated position of the instrument object 40 and/or the accuracy of the mappings between the grandchild virtual space $S_{gc\_endo}$ and the child virtual space $S_{child\_mic}$. For instance, as discussed above, the multidimensional tracking system 100 translates the second observed position $P_{object\_i\_2} \in S_{gc\_endo}$ of the instrument object 40 to the child virtual space $S_{child\_mic}$ to become the second translated position $P_{object\_i\_2}'=(a_{i\_2}', b_{i\_2}', C_{i\_2}') \in S_{child\_mic}$. The multidimensional tracking system 100 can compare the second translated position $P_{object\_i\_2}' \in S_{child\_mic}$ of the instrument object 40 against the first observed position $P_{object\_1}=(a_i, b_i,$ $c_i) \in S_{child\_mic}$ within the same child virtual space $S_{child\_mic}$ and use any positional errors between the second translated position $P_{object\_i\_2}' \in S_{child\_mic}$ and the first observed position $P_{object\_i\_1}$ E $S_{child\_mic}$ for the same object taken at the same or similar timestamp to update one or more positional estimation parameters of the child tracking system 140 or the grandchild tracking system 160, or to update the mapping between the child tracking system 140 and the grandchild tracking system 160.

This example can be extended to anatomical structures as tracked objects; given an expected position of an anatomical structure and one or more observed positions of the anatomical structure, the multidimensional tracking system 100 can update the expected positions of the anatomical structure on the display device 190 and with respect to other tracked objects. This is particularly useful in the context of anatomical shift (ex. "brain sag" in the case of the brain), which is a well described and major pitfall of stereotactic navigation applications. This refers to the event of progressive inaccuracy of a stereotactic navigation system's estimation of real-world locations within imaging, based on gravitational or fluid shifting within the anatomy. The ability for the multidimensional tracking system 100 to represent a patient's surface anatomy in real-time within one or more virtual spaces can allow for modulatory feedback on pre-operative registration of anatomy to offset or otherwise compensate for the inaccuracy experienced throughout a surgical case. In some embodiments, the multidimensional tracking system 100 can incorporate historic data in which a child tracking system 140 (OM) recorded a temporal variation in a position of an anatomical landmark object. Knowledge of temporal variation in positions permits the multidimensional tracking system 100 to apply a machine learning-based model to predict anatomical shift within future cases given repeated or iterative observation of deformations across a plurality of datasets that are either regionally-specific or globally applicable for the subject anatomical structure. While this example was given in terms of cranial surgery, it should be noted that the multidimensional tracking system 100 can be used in the context of other types of surgeries or in the context of non-surgical applications.

Current era operating microscope technology permits adoption of ocular designated cameras (i.e. mounted dual camera visualization of the operative field) which generates stereo video in a 3-dimensional virtual space capable of being viewed in 3 dimensions via a compatible monitor and further permits recording. 3-dimensional video can be captured via recording of two stereo video channels, the differential of which permits an assessment of depth, that are associated to fixed points on the microscope with respect to the parent virtual space $S_V$ that can also include a patient's cross-sectional imaging. In some embodiments, the multidimensional tracking system 100, specifically the operating microscope serving as the child tracking system 140, can utilize a polynomial depth-disparity model to generate the independent child virtual space $S_{child\_mic}$. Knowing the positional relationship between the parent virtual space $S_V$ and the child virtual space $S_{child\_mic}$ permits an overlay of one on the other to permit tracking of objects within the stereo-camera derived field (i.e., from the operating microscope serving as the child tracking system 140) with respect to the patient's cross-sectional imaging.

In one example, through concurrent recording of operating microscope position (and thereby focal point via the knowledge of focal length throughout the procedure) and stereo video from the operating microscope's two dedicated video ocular channels, any relevant physical feature of an object of interest can be tracked in physical space over time. For instance, recording of instrument position relative to the patient's anatomy, permits generation of a dataset for each procedure, where several metrics that describe instrument use can be analyze, including instrument identification, utilization patterns (e.g., frequency of use, duration of use, sequence of use), and technical features (e.g., finger position relative to instrument, apparent tension applied to instrument). These features are all captured in association with the patient's anatomy, thereby permitting calculations of efficiency, errors in instrument use, assignment of risks for complications, predictions of the remaining length of the procedure, or predictive methods of next instrument selection. The metrics of instrument use can be analyzed relative to the progression of Cartesian space navigation, thereby enhancing the educational and academic understanding of surgical instrument efficiency.

In some embodiments, applying machine learning principles to data obtained through instrument tracking relative to a patient's anatomy can enhance the predictive capability of the multidimensional tracking system 100 for a surgeon's technical progression through the surgical approach. For instance, machine-learning guided learning predictions can identify errors in a practitioner's surgical technique (for example, finger position relative to instrument) that when rectified may permit enhanced surgical efficiency. A training dataset educating a machine learning algorithm can be generated based on "master surgeons" within the respective surgical community. This model of training permits enhanced feedback to the learner and suggestions for improvement on a case-by-case basis. The generation and propagation of this instrument tracking dataset can similarly be constructed into a library within which multiple surgeons' data can be housed. This permits surgeon-to-surgeon comparison by the machine learning algorithm to identify differences in technique and can serve to build a foundation of robotic surgical instrument manipulation and technical execution.

Figure 4B:
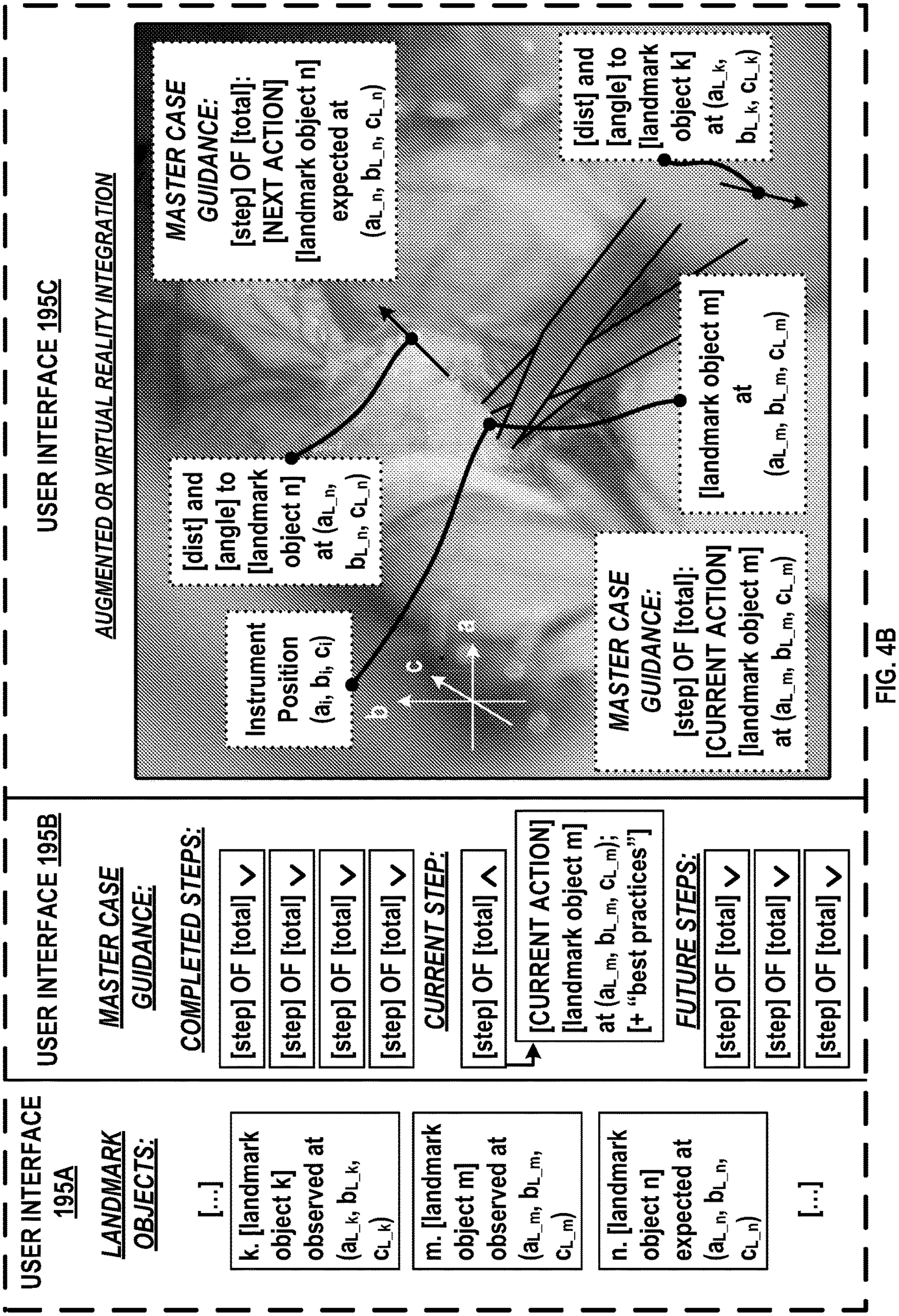
FIG. 4B is a diagram showing an example user interface of the multidimensional tracking system of FIG. 4A that provides master case guidance to a practitioner in an augmented-reality format.

In some embodiments, the multidimensional tracking system 100 can incorporate recollection of one or more "master" cases based on "master surgeons" within the respective surgical community through virtual projection of an object including potential manipulation of the object to a display device 190, which can include augmented reality (AR) display within microscope or other tracking system oculars, projected in physical space, or within a virtual reality (VR) environment. In the example of FIG. 4B, an example display device 190 is illustrated that provides AR-based guidance during a surgical case based on one or more "master" cases. In the example, the display device 190 shows an example field-of-view of the child tracking system 140, which is in some embodiments the operating microscope. The display device 190 can display information related to the case including positions of landmark objects that are relevant to the surgical case by recalling information from one or more similar master cases, such as an action to be taken at each respective step of a plurality of steps with respect to known and expected positions of landmark objects and known positions of instruments and hierarchical tracking sub-systems 110, and can further display directional metrics such as distances and angles to one or more landmark objects relevant to future or past steps. For example, the multidimensional tracking system 100 can determine where one or more objects are relative to a virtual space, such as parent virtual space $S_V$, child virtual space $S_{CHILD}$, or grandchild virtual space $S_{GC}$, and can recall similar master case(s) including information related to one or more actions taken, expected and observed positions of landmark objects, surgical best practices (such as instrument type, relative pressure to be applied, finger positions relative to instrument type, etc.). The multidimensional tracking system 100 can orient the similar master case(s) with respect to a current orientation of the hierarchical tracking sub-systems 110 and the surgical space and can further display information related to the similar master case(s) at the display device 110. This information can be displayed at the same time in more than one fashion, such as a listing of landmark objects as shown in a first user interface 195A, a listing of steps within the surgical case based on the master case(s) in a second user interface 195B, and an AR-based display of relevant information with respect to an observed space in a third user interface 195C, which can be superimposed over a video feed or other captured image as captured by one or more hierarchical tracking sub-systems 110. As shown in the third user interface 195C, the multidimensional tracking system 100 can display information at the display device 190 in an AR or VR environment relevant to past, current, or future steps as correlated to the one or more master case(s).

3. Hierarchical Tracking Sub-Systems

Figure 5:
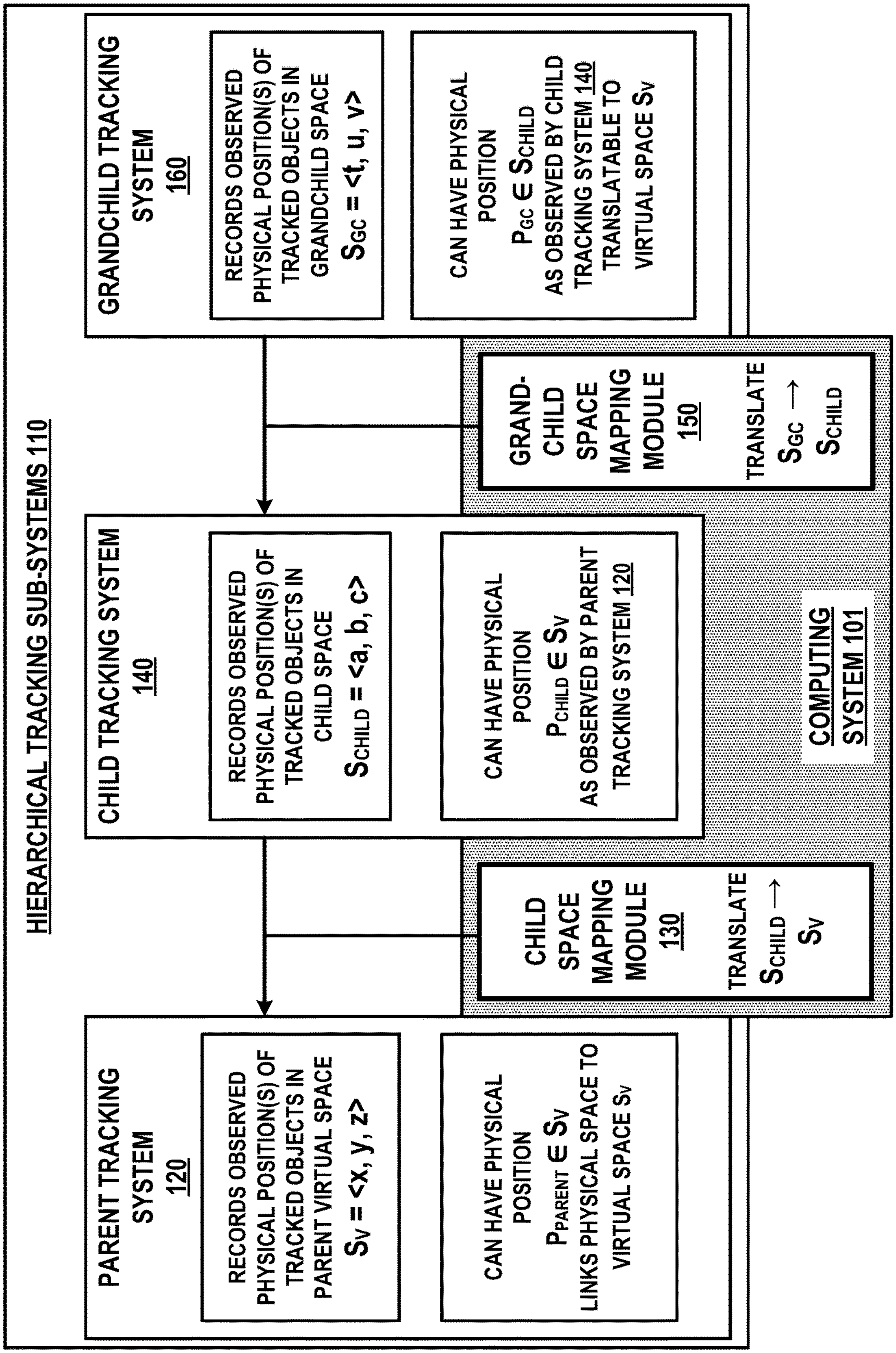
FIG. 5 is a simplified diagram showing the plurality of hierarchical tracking sub-systems of FIG. 1A and a plurality of mapping modules that enable translation between a plurality of virtual spaces defined by the plurality of hierarchical tracking sub-systems.

FIGS. 5-9 collectively illustrate various components of the hierarchical tracking sub-systems 110 of the multidimensional tracking system 100. In particular, FIG. 5 provides an overview of the parent tracking system 120, the child tracking system(s) 140, the child space mapping module 130 that generates and maintains mapping(s) between the parent tracking system 120 and the child system(s) 140, the grandchild tracking system(s) 160, and the grandchild space mapping module 150 that generates and maintains mapping(s) between the child tracking system(s) 140 and the grandchild system(s) 160. The parent tracking system 120 records observed physical position(s) of tracked objects in terms of the parent virtual space $S_V$=<x,y,z> and can have a physical position in the physical space represented in the parent virtual space $S_V$ as $P_{PARENT} \in S_V$. The child tracking system 140 records observed physical position(s) of tracked objects in terms of the child virtual space $S_{CHILD}$=<a,b,c> and can be tracked by the parent tracking system 120; as such, the child tracking system 140 can have a physical position in physical space represented in terms of the parent virtual space $S_V$ as $P_{CHILD} \in S_V$. Optionally, when available and to improve accuracy, the child tracking system 140 can also be tracked by one or more additional child tracking system(s) 140 and/or grandchild system(s) 160 and thus can have additional positions represented in terms of additional child and/or grandchild virtual spaces for comparison with one another. The child space mapping module 130 translates the child virtual space $S_{CHILD}$ to the parent virtual space $S_V$, and also translates the physical position(s) of objects tracked by the child tracking system 140 from the child virtual space $S_{CHILD}$ to the parent virtual space $S_V$ based on a first positional relationship between the child tracking system 140 and the parent tracking system 120. In some embodiments, the child space mapping module 130 and the grandchild space mapping module 150 can be implemented on the computing system 101 in communication with the hierarchical tracking sub-systems 110.

The grandchild tracking system 160 records observed physical position(s) of tracked objects in terms of the grandchild virtual space $S_{GC}$=<t,u,v> and can be tracked by the child tracking system 140; as such, the grandchild tracking system 160 can have a physical position in physical space represented in terms of the child virtual space $S_{CHILD}$ as $P_{GC} \in S_{CHILD}$. Optionally, when available and to improve accuracy, the grandchild tracking system 160 can also be tracked by the parent tracking system 120 and/or can similarly be tracked by one or more additional child tracking system(s) 140 and/or grandchild system(s) 160 and thus can have additional positions represented in terms of additional parent, child and/or grandchild virtual spaces for comparison with one another. The grandchild space mapping module 150 translates the grandchild virtual space $S_{GC}$ to the child virtual space $S_{CHILD}$, and also translates the physical position(s) of objects tracked by the grandchild tracking system 160 from the grandchild virtual space $S_{GC}$ to the child virtual space $S_{CHILD}$ based on a second positional relationship between the grandchild tracking system 160 and the child tracking system 140. The child space mapping module 130 can then translate the translated physical position(s) of objects tracked by the grandchild tracking system 160 to the parent virtual space $S_V$, now that the translated physical position(s) of objects tracked by the grandchild tracking system 160 are available with respect to the child virtual space $S_{CHILD}$.

To permit quantitative association between multiple virtual spaces, a systematic standard can be adopted to ensure accuracy and avoid speculative relativity. Many such units could be applicable for this purpose (e.g., voxels, inches, centimeters, or including but not limited to arbitrary virtual space numerical indicators). Given that the physical world can be represented within various embodiments described herein, one may use the physical units of centimeters, for example. The virtual space transform can be performed, for example, on either identical dimensional systems (e.g., a parent 3-dimensional space encompassing a child 3-dimensional space) or an ascending or declining order of virtual space complexity (e.g., a parent 3-dimensional space encompassing a child 2-dimensional space) with the understanding that by doing so, assumptions within the virtual space could be made that obscure the transform. To accomplish a transform, the multidimensional tracking system 100 must reference a systematic standard for distance (ex. Centimeters) within the child virtual space $S_{CHILD}$ to appropriately transform the child virtual space $S_{CHILD}$ to the parent virtual space $S_V$, assuming parent virtual space $S_V$ is represented in identical units. This would also permit the appropriate representation of objects observed within the child virtual space $S_{CHILD}$ to be translated to a position in the parent virtual space $S_V$.

3.1 Child Space Mapping

Figure 6:
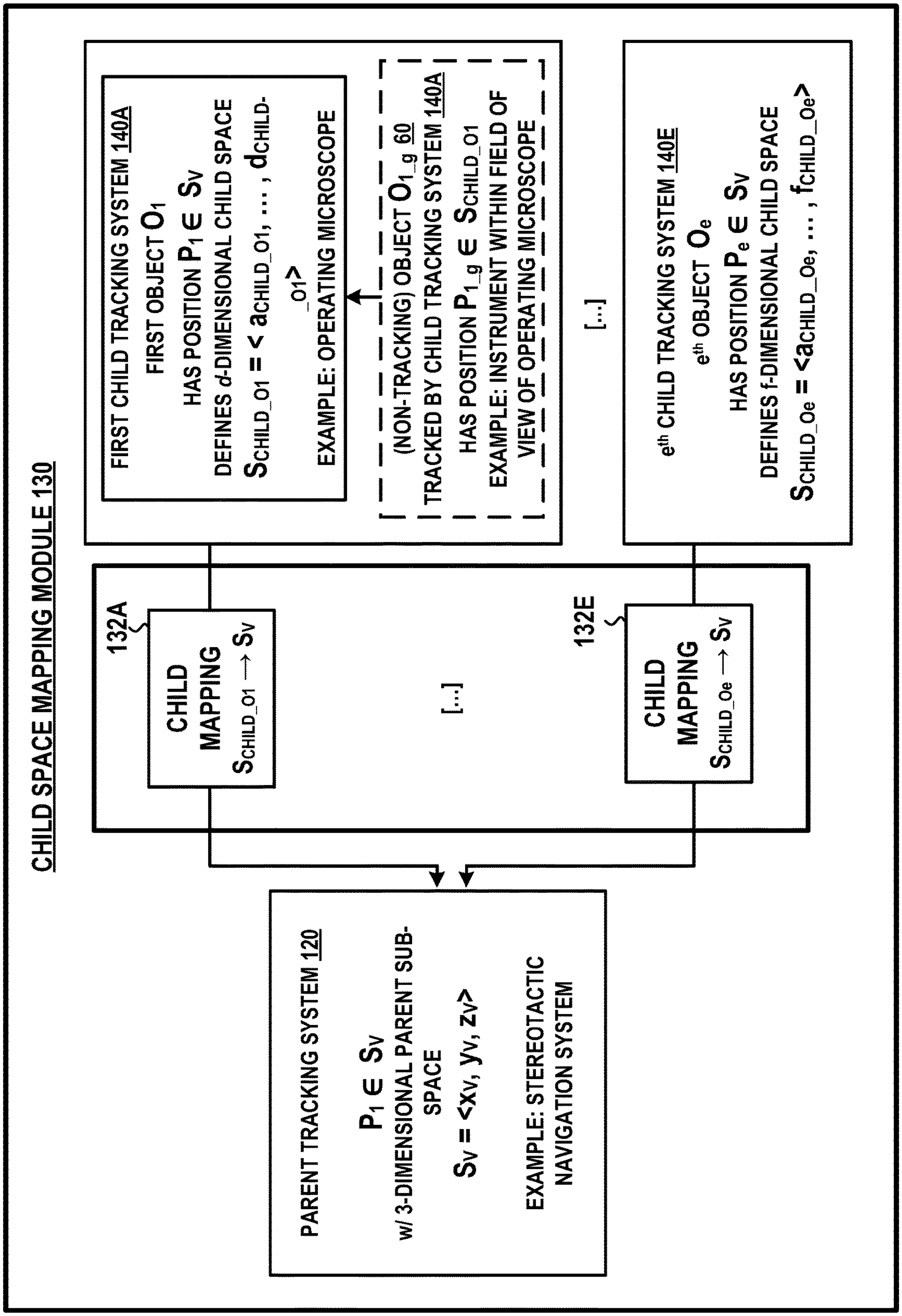
FIG. 6 is a simplified diagram showing an example child vector mapping module of the plurality of mapping modules of FIG. 5 for mapping a child virtual space to a parent virtual space.
Figure 7:
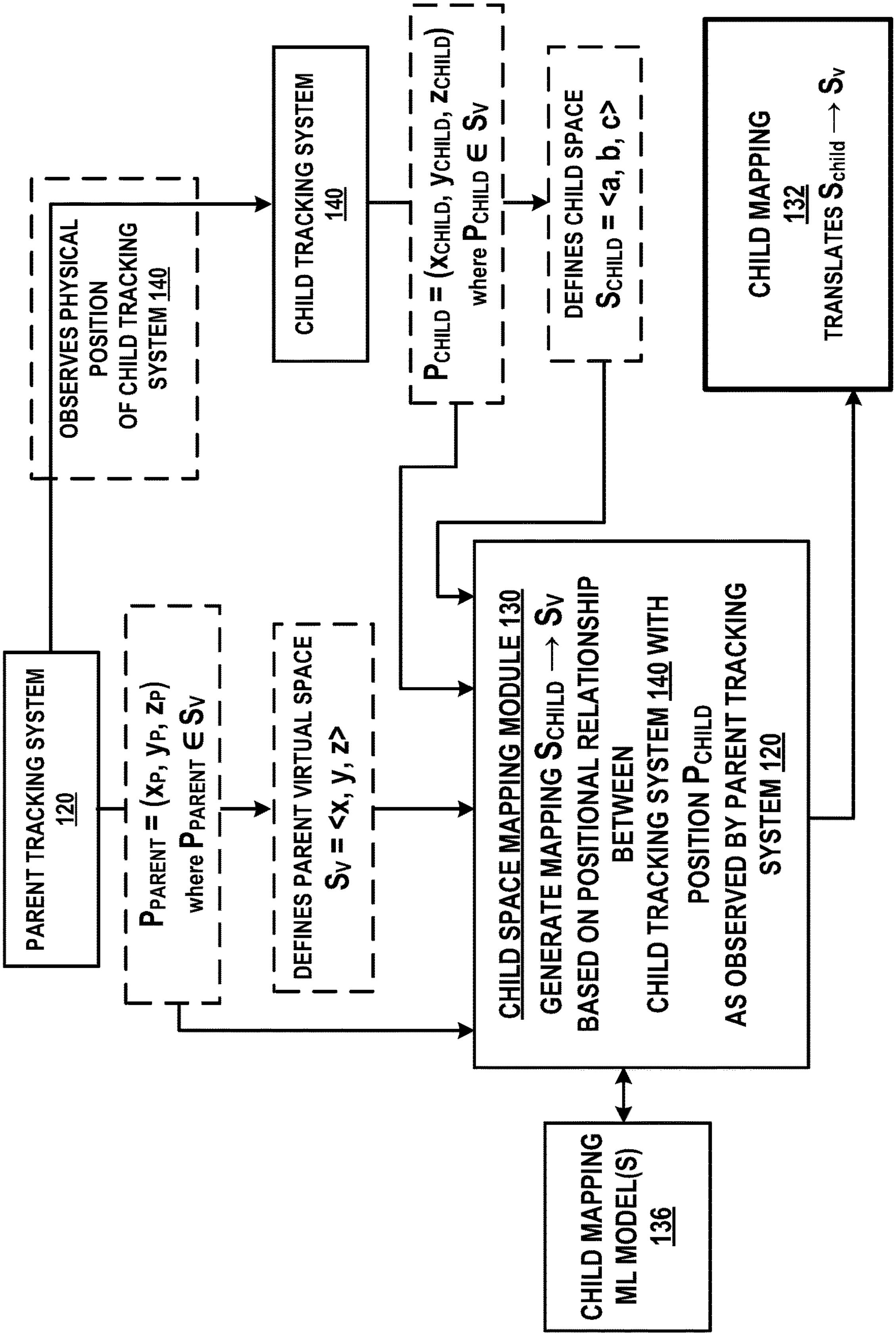
FIG. 7 is a simplified diagram showing generation of a mapping between the child virtual space and the parent virtual space of FIG. 6 based on a first positional relationship between the child tracking system and the parent tracking system.

FIG. 6 illustrates one example of the child space mapping module 130 of the multidimensional tracking system 100. As shown, the child space mapping module 130 includes a plurality of child mappings 132A-132E (collectively, child mappings 132) that each map a respective child tracking system 140 of a plurality of child tracking systems 140A-140E (collectively, a plurality of child tracking systems 140) to a parent tracking system 120. In the example shown, a first child tracking system 140A is also considered a first object $O_1$, has a position $P_1 \in S_V$ observable by the parent tracking system 120, and defines a d-dimensional child virtual space $S_{CHILD\_O1}$=<$a_{CHILD\_O1}$, . . . , $d_{CHILD\_O1}$>. The first child tracking system 140A can track a (non-tracking) object $O_{1\_g}$ 60 that has a position $P_{1\_g} \in S_{CHILD\_O1}$ representative of a physical position in physical space. The child space mapping module 130 provides a first child mapping 132A that maps the d-dimensional child virtual space $S_{CHILD\_O1}$ to the parent virtual space $S_V$. In some embodiments, the first child mapping 132A can include a simple vector mapping that provides a Cartesian offset (if d=3) for translating the first d-dimensional child virtual space $S_{CHILD\_O1}$ and the (non-tracking) object $O_{1\_g}$ 60 with position and orientation defined therein to the parent virtual space $S_V$. In other embodiments, the child space mapping module 130 can "learn" or otherwise infer the first child mapping 132A by observing the positional relationships between the parent tracking system 120 and the first child tracking system 140A and by observing orientations and positions of objects tracked by both the parent tracking system 120 and the first child tracking system 140A using one or more child mapping machine-learning models 136 (FIG. 7). Since the first child tracking system 140A is not necessarily fixed in one position, the child space mapping module 130 can iteratively and continuously update the first child mapping 132A over time. With additional reference to FIG. 4A, one example of a real-world application of the first child tracking system 140A can be an operating microscope, where the parent tracking system 120 can be a stereotactic navigation system and the (non-tracking) object $O_{1\_g}$ 60 can be an instrument within a field-of-view of the first child tracking system 140A.

In the example shown, an $e^{th}$ child tracking system 140E is considered an $e^{th}$ object $O_e$, has a position $P_e \in S_V$ observable by the parent tracking system 120, and defines an f-dimensional child virtual space $S_{CHILD\_Oe}$=<$a_{CHILD\_Oe}$, . . . , $f_{CHILD\_Oe}$>. The child space mapping module 130 provides an $e^{th}$ child mapping 132E that maps the $e^{th}$ f-dimensional child virtual space $S_{CHILD\_Oe}$ to the parent virtual space $S_V$.

Referring to FIG. 7, the child space mapping module 130 generates a child mapping 132 between a child virtual space $S_{CHILD}$ and a parent virtual space $S_V$ for a child tracking system 140 based on the positional relationship between a parent tracking system 120 and the child tracking system 140 having position $P_{CHILD}$ in the parent virtual space $S_V$ as observed by parent tracking system 120. As discussed above, in some embodiments, the child space mapping module 130 can "learn" or otherwise infer the child mapping 132 by observing positional relationships between the parent tracking system 120 and the child tracking system 140 and by observing orientations and positions of objects tracked commonly between the parent tracking system 120 and the child tracking system 140 using one or more child mapping machine-learning models 136. The one or more child mapping machine-learning models 136 can be pre-trained or can be trained on a training dataset that provides examples of correct and incorrect mappings with positions and orientations of various objects. Further, the one or more child mapping machine-learning models 136 can be suited to the specific application. For instance, if the parent tracking system 120 or the child tracking system 140 relies heavily on optical methods for object detection and position estimation, then the one or more child mapping machine-learning models 136 should be well-suited for image-based object detection and position estimation. The one or more child mapping machine-learning models 136 can "learn" the correct child mapping 132 between the child virtual space $S_{CHILD}$ and the parent virtual space $S_V$ based on observed objects that are common to both spaces and based on known and/or observable positional relationships between the between the parent tracking system 120 and the child tracking system 140. Child mappings 132 can be verified for correctness by translating object positions to and from the child virtual space $S_{CHILD}$ and comparing results with verified, observable object positions. Further, since the child tracking system 140 is not necessarily fixed in one position, the child space mapping module 130 can iteratively and continuously update the child mapping 132. In some embodiments, mapping generation by the child space mapping module 130 can be aided by the one or more marker objects 113 (FIGS. 3A-3D) that provide universal reference points for accurate translation between virtual spaces.

In some embodiments, the multidimensional tracking system 100 can enable a practitioner to initiate "re-mapping" of a child virtual space $S_{CHILD}$ with respect to the parent virtual space $S_V$ on-demand rather than through continuous re-mapping and orientation. This can involve placement of a "test" marker object within the environment to define a current association between the parent tracking system 120 and the child tracking system 140. For example, a marker object 113 for this purpose can include a probe with a frame whose position and orientation are tracked by the parent tracking system 120 similar to the stereotactic frame 30 of FIG. 4A. the probe can have a uniquely identifiable tooltip whose position the child tracking system 140 can easily and accurately observe in the child virtual space $S_{CHILD}$. The child space mapping module 130 could then associate the probe between the parent tracking system 120 and the child tracking system 140, and the practitioner can adjust the virtual position of the tool within the parent virtual space $S_V$ or the child virtual space $S_{CHILD}$ if an observable difference is present.

3.2 Grandchild Space Mapping

Figure 8:
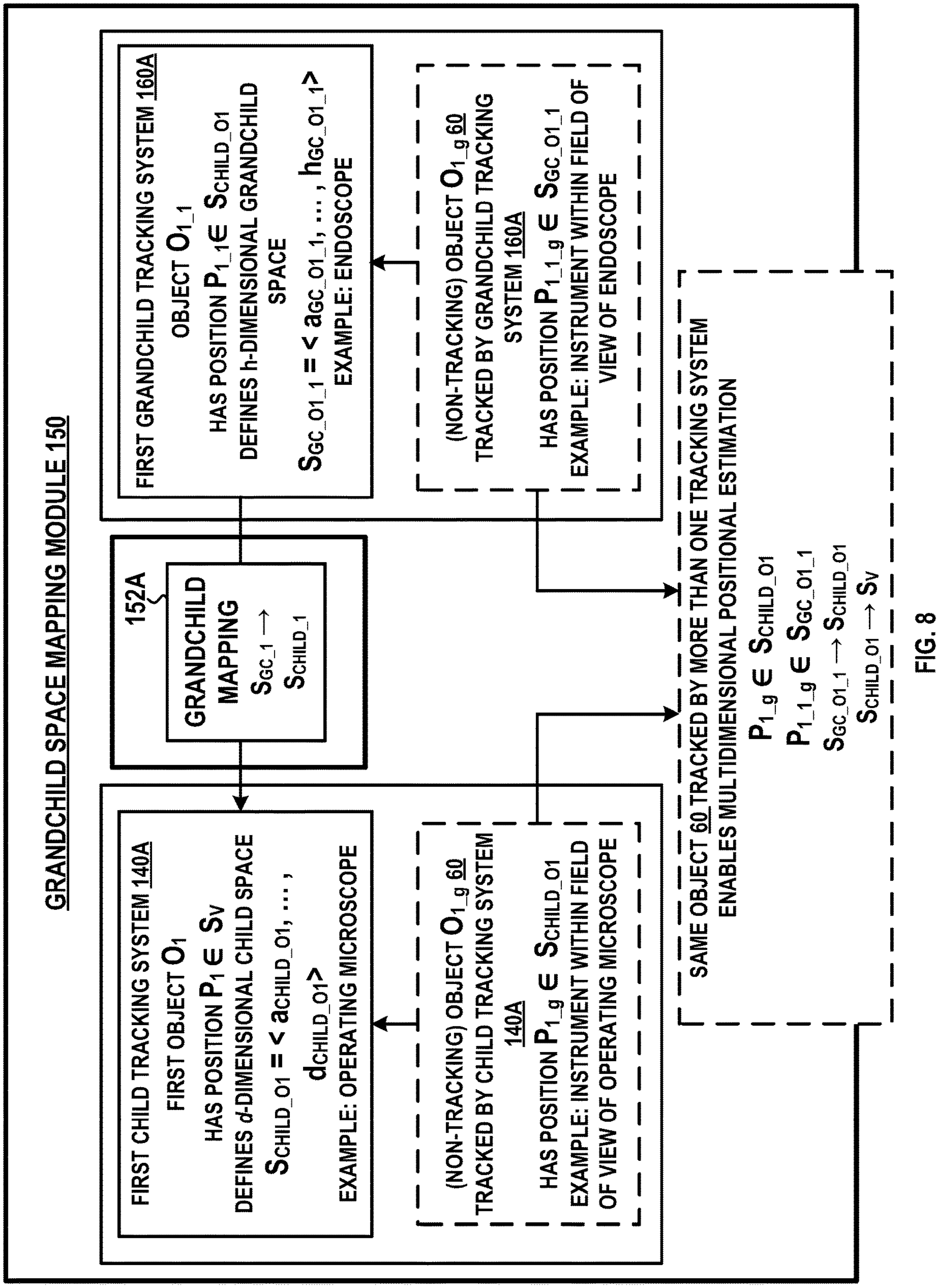
FIG. 8 is a simplified diagram showing an example grandchild space mapping module of the plurality of mapping modules of FIG. 5 for mapping a grandchild virtual space to a child virtual space.

FIG. 8 illustrates one example of the grandchild space mapping module 150 of the multidimensional tracking system 100. As shown, the grandchild space mapping module 150 includes at least one grandchild mapping 152 that maps a respective grandchild tracking system 160 to a parent tracking system 120. In the example shown, a first grandchild tracking system 160A is also considered an object $O_{1\_1}$, has a position $P_{1\_1} \in S_{CHILD\_O1}$ observable by the first child tracking system 140A, and defines an h-dimensional child virtual space $S_{GC\_O1\_1}$=<$A_{GC\_O1\_1}$, . . . , $h_{GC\_O1\_1}$>. The grandchild tracking system 160A can track one or more objects, which in this example can include the (non-tracking) object $O_{1\_g}$ 60 that can have an additional position $P_{1\_1\_g} \in S_{GC\_O1\_1}$ while still having the same physical position in physical space. The grandchild space mapping module 150 provides a first grandchild mapping 152A that maps the first h-dimensional grandchild virtual space $S_{GC\_O1\_1}$ to the child virtual space $S_{CHILD\_O1}$. In the example of the (non-tracking) object $O_{1\_g}$ 60, which can be tracked by both the first child tracking system 140A (FIG. 6) and the first grandchild tracking system 160A, the multidimensional tracking system 100 allows comparison of the positions $P_{1\_1\_g} \in S_{GC\_O1\_1}$, $P_{1\_g} \in S_{CHILD\_O1}$ of the (non-tracking) object $O_{1\_g}$ 60 which are both representative of the physical position of the (non-tracking) object $O_{1\_g}$ 60 in the physical space to update one or more positional estimation parameters of the child tracking system 140A or the grandchild tracking system 160A, or to update the grandchild mapping 152A between the child tracking system 140A and the grandchild tracking system 160A.

Figure 9:
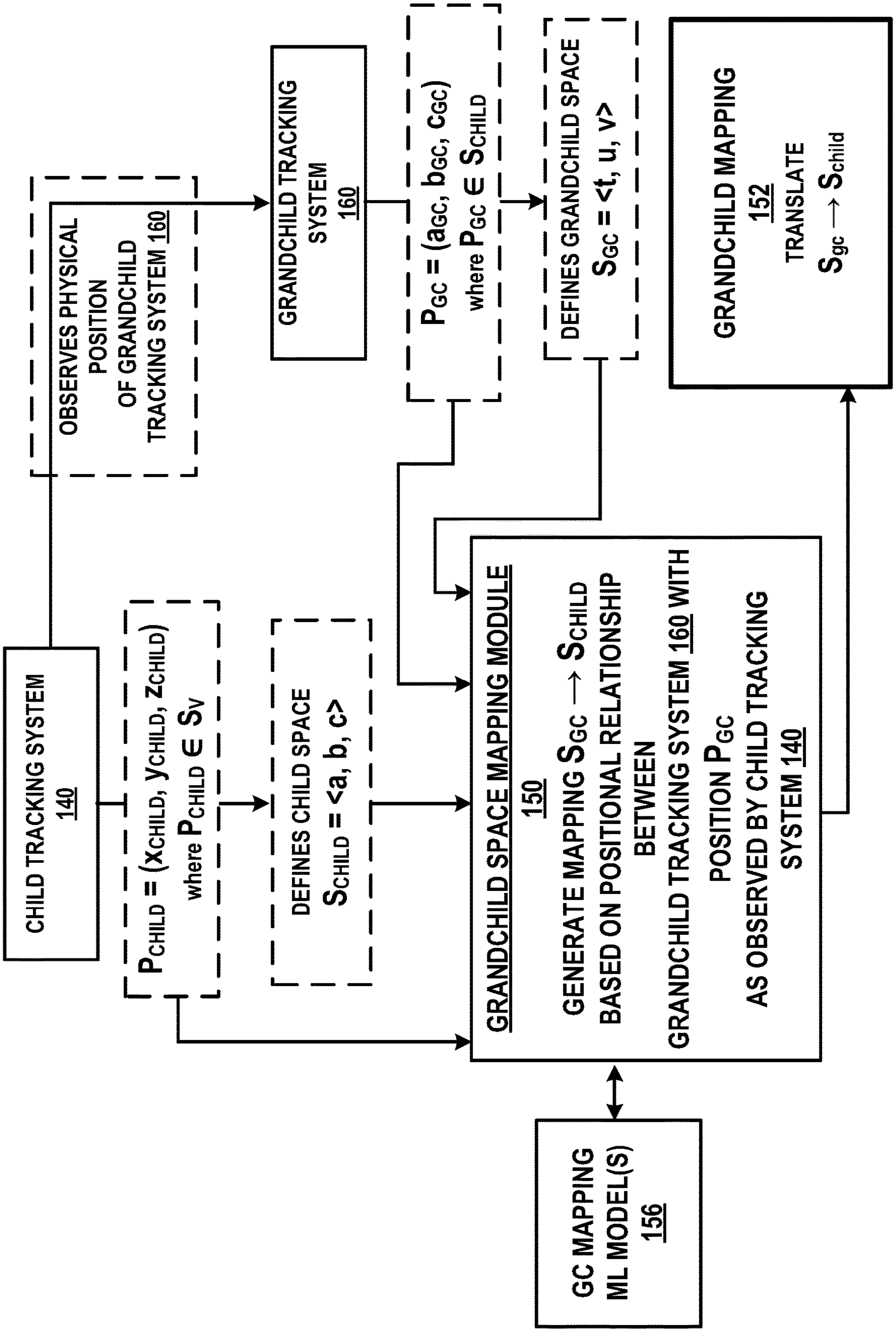
FIG. 9 is a simplified diagram showing generation of a mapping between the grandchild virtual space and the child virtual space of FIG. 8 based on a second positional relationship between the grandchild tracking system and the child tracking system.

In some embodiments, the grandchild mapping 152A can include a simple vector mapping that provides a Cartesian offset (if h=3) for translating the h-dimensional grandchild virtual space $S_{GC\_O1\_1}$ and the position and orientation of the object $O_{1\_g}$ 60 to the parent virtual space $S_V$. In other embodiments, the grandchild space mapping module 150 can "learn" or otherwise infer the grandchild mapping 152A by observing the positional relationships between the first child tracking system 140A and the grandchild tracking system 160A and by observing orientations and positions of objects tracked by both the child tracking system 140A and the grandchild tracking system 160A using one or more grandchild mapping machine-learning models 156 (FIG. 9). Since the first grandchild tracking system 160A and the first child tracking system 140A are not necessarily fixed in one position, the grandchild space mapping module 150 can iteratively and continuously update the first grandchild mapping 152A over time.

Referring to FIG. 9, the grandchild space mapping module 150 generates a grandchild mapping 152 between a grandchild virtual space $S_{GC}$ and a child virtual space $S_{CHILD}$ for a grandchild tracking system 160 based on the positional relationship between a child tracking system 140 and the grandchild tracking system 160 having position $P_{GC}$ in the child virtual space $S_{CHILD}$ as observed by child tracking system 140. As discussed above, in some embodiments, the grandchild space mapping module 150 can "learn" or otherwise infer the grandchild mapping 152 by observing the positional relationships between the child tracking system 140 and the grandchild tracking system 160 and by observing orientations and positions of objects tracked commonly between the child tracking system 140 and the grandchild tracking system 160 using one or more grandchild mapping machine-learning models 156. The one or more grandchild mapping machine-learning models 156 can be pre-trained or can be trained on a training dataset that provides examples of correct and incorrect mappings with positions and orientations of various objects. Further, the one or more grandchild mapping machine-learning models 156 can be suited to the application. For instance, if the parent tracking system 120, the child tracking system 140, or the grandchild tracking system 160 relies heavily on optical methods for object detection and position estimation, then the one or more grandchild mapping machine-learning models 156 should be well-suited for image-based object detection and position estimation. The one or more grandchild mapping machine-learning models 156 can "learn" the correct grandchild mapping 152 between the grandchild virtual space $S_{GC}$ and the child virtual space $S_{CHILD}$ based on observed objects that are common to both spaces and based on known and/or observable positional relationship between the between the grandchild tracking system 160 and the child tracking system 140. Grandchild mappings 152 can be verified for correctness by translating object positions to and from the grandchild virtual space $S_{GC}$ and comparing results with verified, observable object positions. Further, since the grandchild tracking system 160 and the child tracking system 140 are not necessarily fixed in one position, the grandchild space mapping module 150 can iteratively and continuously update the grandchild mapping 152. In some embodiments, mapping generation by the grandchild space mapping module 150 can be aided by the one or more marker objects 113 (FIGS. 3A-3D) that provide universal reference points for accurate translation between virtual spaces.

Similar to that of the child virtual space $S_{CHILD}$, in some embodiments, the multidimensional tracking system 100 can enable a practitioner to initiate "re-mapping" of a grandchild virtual space $S_{GC}$ with respect to the child virtual space $S_{CHILD}$ or the parent virtual space $S_V$ on-demand rather than through continuous re-mapping and orientation. This can involve placement of a "test" marker object within the environment to define a current association between the grandchild tracking system 160 and the child tracking system 140 or the parent tracking system 120. For example, a marker object 113 for this purpose can include a probe with a frame whose position and orientation are tracked by the child tracking system 140 or the parent tracking system 120 similar to the stereotactic frame 30 of FIG. 4A. the probe can have a uniquely identifiable tooltip whose position the grandchild tracking system 160 can easily and accurately observe in the grandchild virtual space $S_{GC}$. The grandchild space mapping module 150 could then associate the probe between the parent tracking system 120 and the child tracking system 140, and the practitioner can adjust the virtual position of the tool within the parent virtual space $S_V$, the child virtual space $S_{CHILD}$, or the grandchild virtual space $S_{GC}$ if an observable difference is present.

3.3 Error Correction

Figure 10:
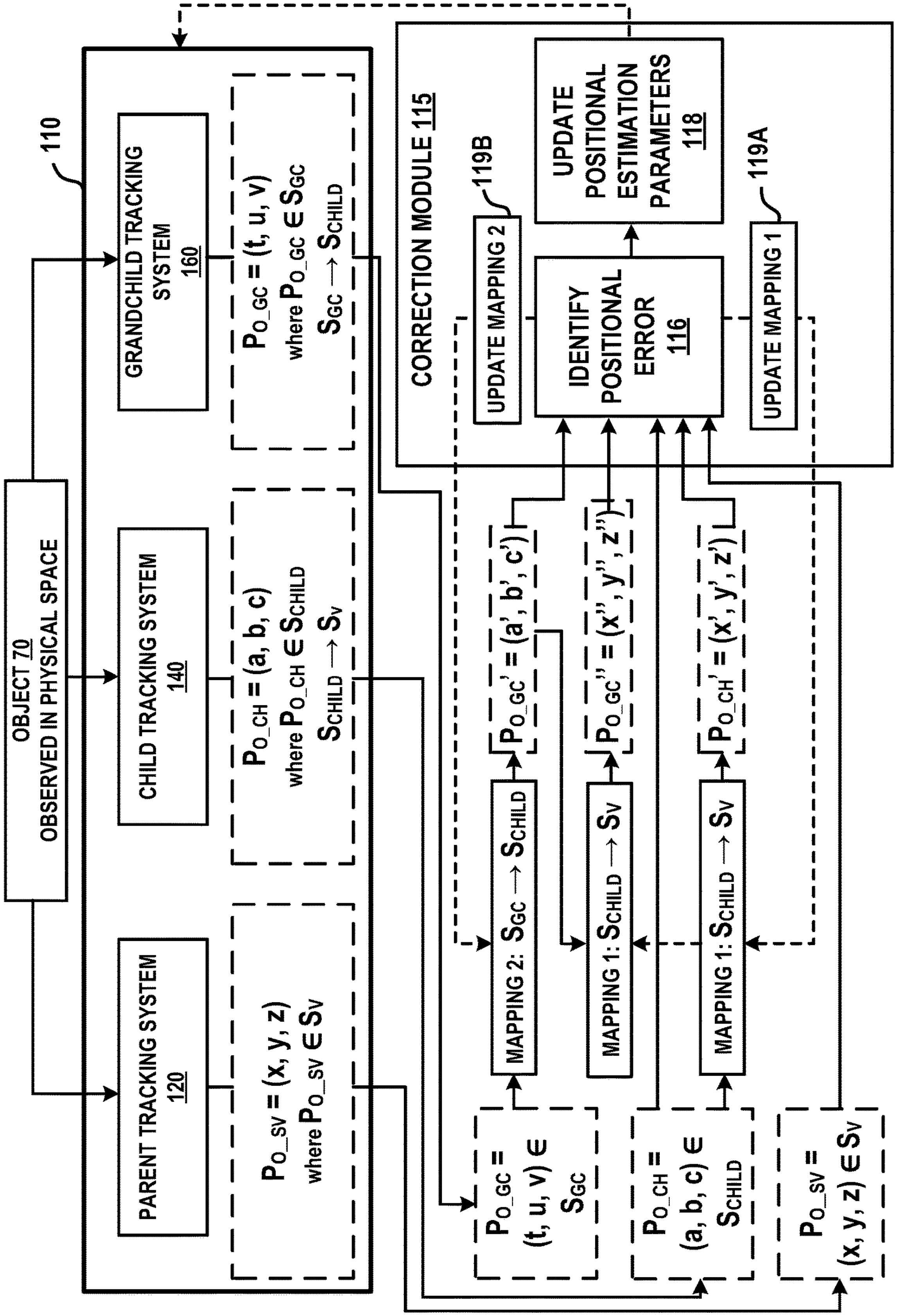
FIG. 10 is a diagram showing error correction of the system of FIG. 1A based on discrepancies between translated positions and actual observed positions of a tracked object.
Figure 11:
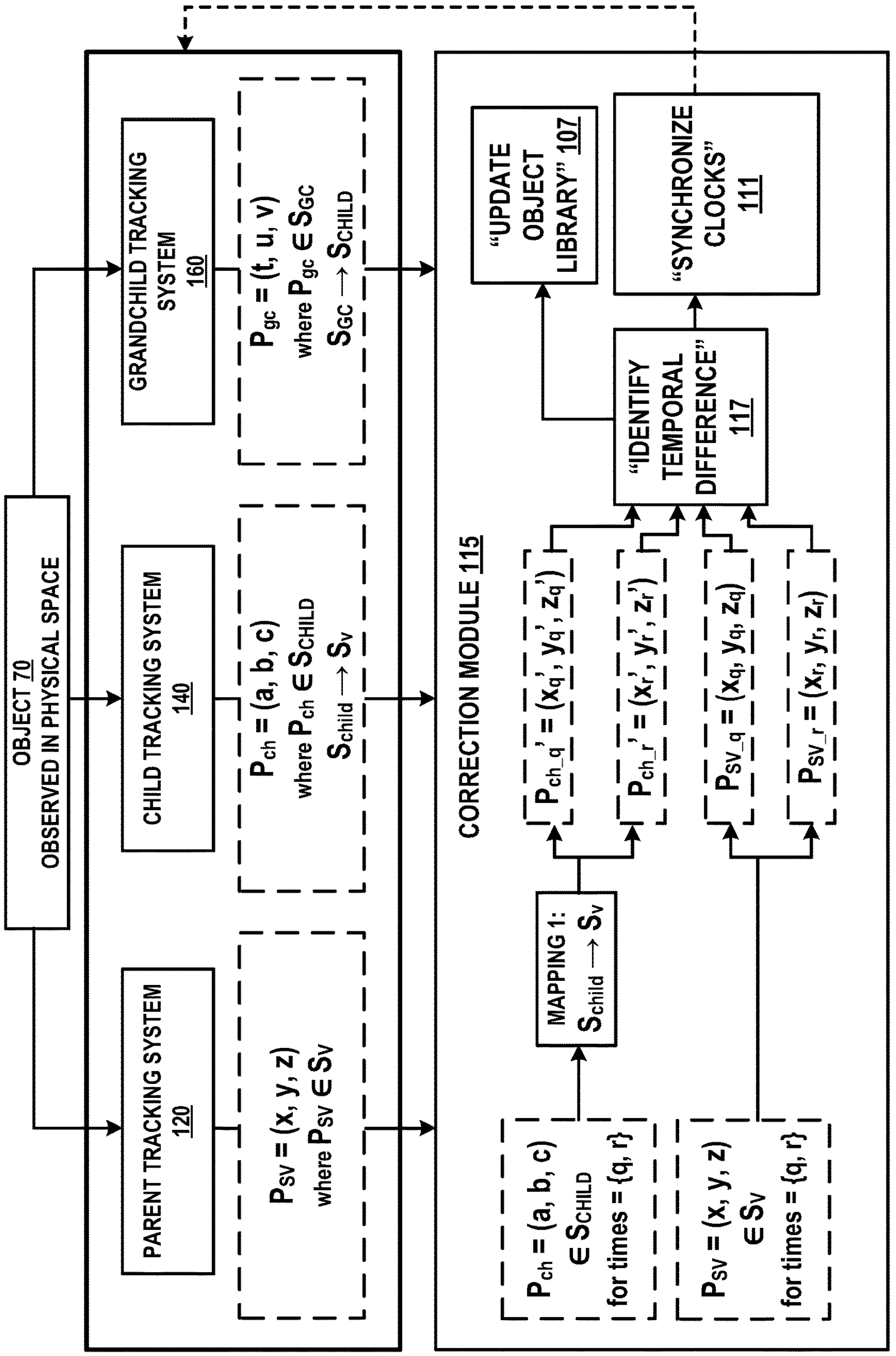
FIG. 11 is a diagram showing error correction of the system of FIG. 1A based on discrepancies between observed positions of a tracked object across one or more timestamps.
Figure 12:
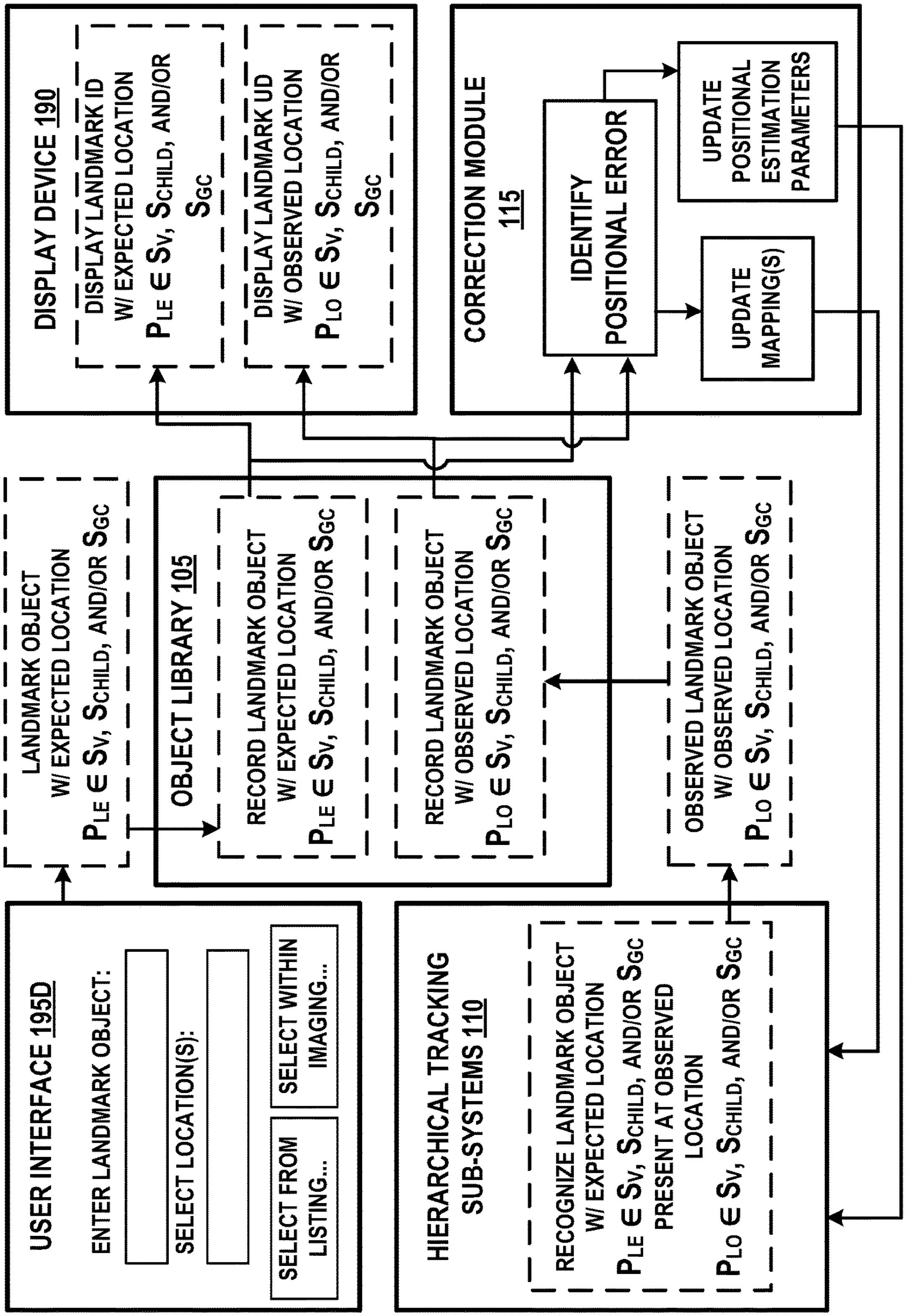
FIG. 12 is a diagram showing error correction of the system of FIG. 1A based on registration and observation of landmark objects.

Referring to FIGS. 10-12, the multidimensional tracking system 100 can include the correction module 115 that enables correction of one or more positional estimation parameters or one or more mappings of the hierarchical tracking sub-systems 110 based on positional errors and temporal differences observable between observed positions, translated positions, and/or expected positions of objects. For instance, FIG. 10 demonstrates correction of one or more positional estimation parameters or one or more mappings of the hierarchical tracking sub-systems 110 based on positional errors. As shown, all three of the hierarchical tracking sub-systems 110 observe a physical position of an object 70 in the physical space and record their own observed positions of the object 70 in their respective virtual spaces. In particular, the parent tracking system 120 records an observed position $P_{o\_SV}$=(x, y, z) of the object 70 in the parent virtual space $S_V$, the child tracking system 140 records an observed position $P_{O\_CHILD}$=(a, b, c) of the object 70 in the child virtual space $S_{CHILD}$, and the grandchild tracking system 160 records an observed position $P_{O\_GC}$=(t, u, v) of the object 70 in the grandchild virtual space $S_{GC}$. The correction module 115 identifies positional errors between observed positions and translated positions and updates one or more positional estimation parameters and/or one or more mappings accordingly. In some embodiments, error correction by the correction module 115 can be aided by the one or more marker objects 113 (FIGS. 3A-3D) that provide universal reference points for accurate positional estimation and translation between virtual spaces.

Referring to FIG. 10, the correction module 115 can include an "identify positional error" block 116 that compares positions of the object 70 across one or more virtual spaces including observed positions and translated positions and determines which hierarchical tracking sub-system 110 has an error based on which translated or observed positions are correct and which translated or observed positions are incorrect, and can also include an "identify temporal difference" block 117 of the correction module 115 that identifies shifting of landmark objects over time based on observed positions taken across one or more timestamps from the hierarchical tracking sub-systems 110. The correction module 115 can also include an "update positional estimation parameters" block 118 that signals to a corresponding hierarchical tracking sub-system 110 to update their positional estimation parameters, which can include introducing a compensatory value or re-calibrating the corresponding hierarchical tracking sub-system 110 based on the positional error. Further, the correction module 115 can also include one or more "update mapping" blocks 119A and 119B (collectively, "update mapping" block 119, but can include as many instances as there are mappings within the multidimensional tracking system 100).

3.4 Identifying Positional Errors

As shown with continued reference to FIG. 10, the observed position $P_{O\_GC}$=(t, u, v) $\in S_{GC}$ as observed by the grandchild tracking system 160 can first be translated to the child virtual space $S_{CHILD}$ based on a second mapping that relates the grandchild virtual space $S_{GC}$ to the child virtual space $S_{CHILD}$ (e.g., $S_{GC} \rightarrow S_{CHILD}$). The result of this translation is translated position $P_{O\_GC}'=(a', b', c') \in S_{CHILD}$, representative of a translated position of the object 70 as observed by the grandchild tracking system 160 and translated to the child virtual space $S_{CHILD}$. An "identify positional error" block 116 of the correction module 115 can directly compare the translated position $P_{O\_GC}' \in S_{CHILD}$ from the grandchild tracking system 160 directly with the observed position $P_{O\_CHILD} \in S_{CHILD}$ as observed by the child tracking system 140.

The translated position $P_{O\_GC}' \in S_{CHILD}$ from the grandchild tracking system 160 can then be translated to the parent virtual space $S_V$ based on a first mapping that relates the child virtual space $S_{CHILD}$ to the parent virtual space $S_V$ (e.g., $S_{CHILD} \rightarrow S_V$). The result of this translation is twice-translated position $P_{O\_GC}''=(x'', y'', z'') \in S_V$, representative of a translated position of the object 70 observed by the grandchild tracking system 160 and translated to the parent virtual space $S_V$ through the intermediate child virtual space $S_{CHILD}$. The "identify positional error" block 116 of the correction module 115 can directly compare the twice-translated position $P_{O\_GC}''=(x'', y'', z'') \in S_V$ from the grandchild tracking system 160 with the observed position $P_{O\_PARENT} \in S_V$ as observed by the parent tracking system 120.

Similarly, the observed position $P_{O\_CHILD}=(a, b, c) \in S_{CHILD}$ as observed by the child tracking system 140 can be translated to the parent virtual space $S_V$ based on the first mapping that relates the child virtual space $S_{CHILD}$ to the parent virtual space $S_V$ (e.g., $S_{CHILD} \rightarrow S_V$). The result of this translation is translated position $P_{O\_CHILD}'=(x', y', z') \in S_V$, representative of a translated position of the object 70 as observed by the grandchild tracking system 160 and translated to the parent virtual space $S_V$. The "identify positional error" block 116 of the correction module 115 can directly compare the translated position $P_{O\_CHILD}' \in S_V$ from the child tracking system 140 with the observed position $P_{O\_PARENT} \in S_V$ as observed by the parent tracking system 120.

In some embodiments, the multidimensional tracking system 100 can also maintain a third mapping that bypasses the intermediate child virtual space $S_{CHILD}$ and directly maps the grandchild virtual space $S_{GC}$ to the parent virtual space $S_V$ (e.g., $S_{GC} \rightarrow S_V$). The result of this translation can be a translated position $P_{O\_GC\_to\_SV}=(x', y', z')$, representative of a translated position of the object 70 as observed by the grandchild tracking system 160 and translated to the parent virtual space $S_V$ independent of the child virtual space $S_{CHILD}$. The "identify positional error" block 116 of the correction module 115 can directly compare the translated position $P_{O\_GC\_to\_SV} \in S_V$ from the grandchild tracking system 160 with the translated position $P_{O\_CHILD}' \in S_V$ from the child tracking system 140 and the observed position $P_{O\_PARENT} \in S_V$ as observed by the parent tracking system 120. In the hypothetical example of FIG. 3A, the grandchild tracking system 160 and the parent tracking system 120 can optionally observe one another and the third mapping can be generated based on mutual observation independent of the child tracking system 140. However, in other examples in which the grandchild tracking system 160 and the parent tracking system 120 do not directly observe one another, then the multidimensional tracking system 100 can infer the third mapping between the grandchild tracking system 160 to the parent tracking system 120 through mutual observation of one or more objects, which can include the one or more marker objects 113 (FIGS. 3A-3D).

As such, comparing observed positions of objects as observed by the plurality of hierarchical tracking sub-systems 110 and translating positions between a plurality of spaces provides additional dimensionality that enables the multidimensional tracking system 100 to examine whether a discrepancy exists between the positional estimation parameters of the hierarchical tracking sub-systems 110 or the mappings between hierarchical tracking sub-systems 110, and for which hierarchical tracking sub-system 110 has the error. As discussed above, this process can be aided by the one or more marker objects 113 (FIGS. 3A-3D) that provide universal reference points for accurate positional estimation and translation between virtual spaces.

Once the "identify positional error" block 116 of the correction module 115 has identified an error between one or more observed positions and/or translated positions from the hierarchical tracking sub-systems 110, then "identify positional error" block 116 can determine which hierarchical tracking sub-system 110 has an error based on which translated or observed positions are correct and which translated or observed positions are incorrect. In some embodiments, the "identify positional error" block 116 further determines whether the error is a translation error (indicating an outdated or inaccurate mapping between two or more hierarchical tracking sub-systems 110 leading to an erroneous translated position), whether the error is an estimation error (indicating that the associated hierarchical tracking sub-system 110 is not correctly estimating positions, leading to an erroneous observed position), or both.

As such, the correction module 115 updates the mappings (e.g., by an "update mapping 1" block 119A and/or an "update mapping 2" block 119B) and/or one or more positional estimation parameters (e.g., by an "update positional estimation parameters" block 118) of the associated hierarchical tracking sub-system 110 (e.g., the grandchild tracking system 160, the child tracking system 140 and/or the parent tracking system 120) based on the positional error. This could include total re-calibration of the associated hierarchical tracking sub-system 110 and/or re-generating one or more mappings (e.g., child mapping(s) 132, grandchild mapping(s) 152 of FIGS. 6 and 8) maintained by the child space mapping module 130 or the grandchild space mapping module 150 (FIG. 1A).

In some embodiments, if the mappings are generated using the one or more child mapping machine-learning models 136 (FIG. 7) or the one or more grandchild mapping machine-learning models 156 (FIG. 9), then the "update mapping 1" block 119A and/or the "update mapping 2" block 119B can update one or more parameters of the one or more child mapping machine-learning models 136 or the one or more grandchild mapping machine-learning models 156 based on the positional error. Similarly, if any of the hierarchical tracking sub-systems 110 use a machine learning model to determine observed positions of objects, then the "update positional estimation parameters" block 118 can instruct the associated hierarchical tracking sub-systems 110 to update or re-calibrate one or more parameters of the machine learning model.

3.5 Identifying Temporal Differences

Similarly, as shown in FIG. 11, the correction module 115 can identify one or more temporal differences between observed positions and/or translated positions of one or more landmark objects taken at a first timestamp (e.g., time=q) and observed positions and/or translated positions of one or more landmark objects taken at a second timestamp (e.g., time=r) to determine or otherwise characterize anatomical shift of the one or more landmark objects. Once an "identify temporal difference" block 117 of the correction module 115 has identified a difference between positional values observed for the same landmark object across one or more timestamps from the hierarchical tracking sub-systems 110, then the "identify temporal difference" block 117 can determine whether anatomical shift has occurred for a landmark object. Alternatively, if there exists an inconsistency between translated values or observed values between hierarchical tracking sub-systems 110, then the "identify temporal difference" block 117 would be able to identify whether anatomical shift has occurred or if a synchronization error between hierarchical tracking sub-systems 110 exists based on which translated or observed positions have larger or smaller discrepancies between values taken between timestamps. As such, if necessary, the correction module 115 updates the expected and/or observed locations of the associated landmark object within the object library 105 at an "update object library" block 107 and/or re-synchronizes the associated hierarchical tracking sub-systems 110 at a "synchronize clocks" block 111.

3.6 Landmark Object Correction

With reference to FIG. 12, in some embodiments, the multidimensional tracking system 100 can track a landmark object that has an expected position in physical space and update the expected position based on an observed position of the landmark object. As discussed, in some embodiments, expected positions of landmark objects can be initially obtained through observation of landmark object positions as recorded within logs and object libraries across a plurality of cases. Further, in some embodiments, historical expected positions of landmark objects can be correlated to a current case using one or more machine learning models that predict shifting of landmark objects given repeated or iterative observation of similar deformations and shift across a plurality of datasets that are either regionally specific or globally applicable for the subject landmark object. This would be particularly useful in the context of microsurgical applications, for instance, a landmark object can be an anatomical structure and the multidimensional tracking system 100 can identify an expected position of the anatomical structure within cross-sectional imaging or within a model of the surgical space, where the expected position can be defined with respect to the parent virtual space $S_V$. Keeping track of the landmark object and regularly updating and displaying the position of the landmark object with respect to one or more virtual spaces can help practitioners avoid mistakes. The multidimensional tracking system 100 can include a user interface 195D in which a user can enter a landmark object identifier representative of a landmark object and an expected position of the landmark object. The expected position of the landmark object can be defined within one or more virtual spaces, such as parent virtual space $S_V$, and can be obtained through the user interface 195D by displaying the parent virtual space $S_V$ and corresponding imaging of an object or a region within the parent virtual space $S_V$ at the display device 190 and receiving the expected position with respect to the displayed parent virtual space $S_V$; for instance, a surgical space or an image of a patient. The multidimensional tracking system 100 can store the landmark object identifier and corresponding expected position $P_{LE}$ in the object library 105, where the expected position $P_{LE}$ is within parent virtual space $S_V$, child virtual space $S_{CHILD}$, and/or grandchild virtual space $S_{GC}$. In some embodiments, the object library 105 and can also translate the expected position $P_{LE}$ to other virtual spaces for viewing with respect to the other virtual spaces, and the display device 190 can display the landmark identifier at the expected position $P_{LE}$ in the parent virtual space $S_V$ or any of the other virtual spaces as maintained within the object library 105.

In some embodiments, the hierarchical tracking sub-systems 110 can recognize a landmark object near the expected location $P_{LE} \in S_V$, $S_{CHILD}$, and/or Sec and can record an observed location of the landmark object PLO $\in$ $S_V$, $S_{CHILD}$, and/or Sec within the object library 105 with respect to the virtual space defined by whichever hierarchical tracking sub-system 110 observes the landmark object. The multidimensional tracking system 100 can optionally implement one or more machine learning models (not shown) for landmark object recognition by the hierarchical tracking sub-systems 110. In some embodiments, the object library 105 can also translate the observed position $P_{LO}$ to other virtual spaces for viewing at the display device 190 with respect to the other virtual spaces and for accuracy verification. The display device 190 can update the landmark identifier to show at the observed position $P_{LO}$ as updated within the object library 105 and can also show a translated position $P_{LO}$ in the parent virtual space $S_V$ or any of the other virtual spaces as maintained within the object library 105. The correction module 115 can verify the observed position $P_{LO}$ across one or more of the hierarchical tracking sub-systems 110 through translation to a plurality of virtual spaces defined by the hierarchical tracking sub-systems 110 and subsequent comparison of translated position with observed positions as originally obtained within each respective virtual space of the plurality of virtual spaces. The correction module 115 can identify positional errors with respect to one or more observed position(s) of the landmark object, and update mappings and/or positional estimation parameters accordingly if a discrepancy exists between the one or more observed position(s) of the landmark object. Once the observed position $P_{LO}$ of the landmark object has been verified, then the observed position $P_{LO}$ can become the new expected location $P_{LE}$. As discussed in a previous section with reference to FIG. 1B, the object library 105 can maintain the log 106 that can include past and present expected locations of the landmark object to provide practitioners with an idea of how the position of the landmark object changes over time. This can be done in conjunction with the "identify temporal difference" block 117 of the correction module 115 discussed above that compares observed positions for landmark objects across timestamps during a procedure to ensure that temporal differences are due to actual shifting positions of landmark objects rather than synchronization errors between the hierarchical tracking sub-systems 110. For surgical applications, this can be very useful in anticipating and correcting expectations for shifting anatomical structures during a procedure. In some embodiments, the multidimensional tracking system 100 can display an alert at the display device 190 or another output device to inform a user when the observed position $P_{LO}$ deviates from the expected location $P_{LE}$ by a certain value, or when the expected location $P_{LE}$ is updated by a significant value.

3.7 Correlating Cross-sectional Imaging with Parent Virtual Space

Figure 13:
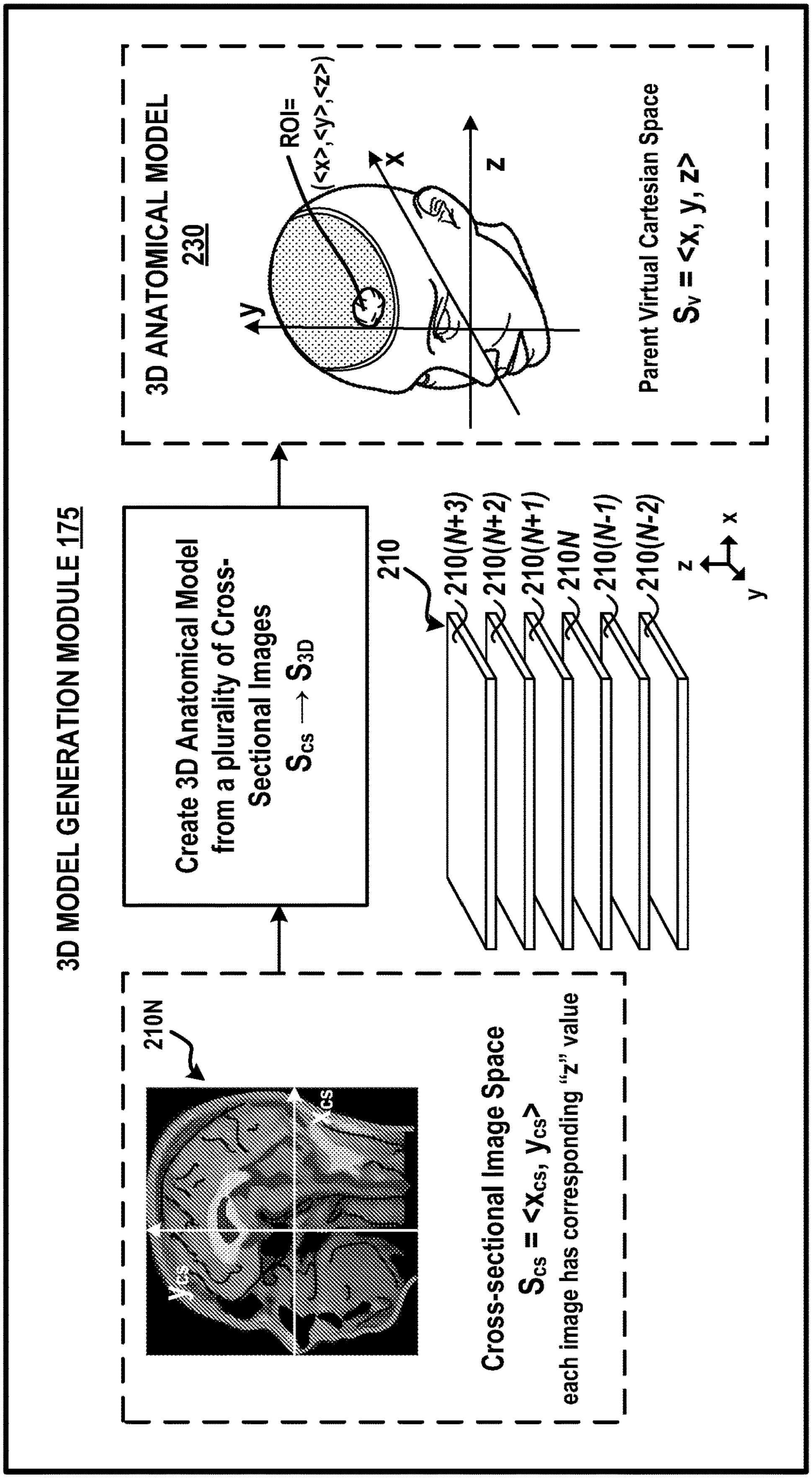
FIG. 13 is a diagram showing a 3D model generation module of the system of FIG. 1A that creates a virtual 3D model based on cross-sectional imaging.

In some embodiments, the display device 190 can display cross-sectional imaging for a space or object, such as a cross-sectional image of a plurality of cross-sectional images that show patient anatomy. In some embodiments, with reference to FIG. 13, the 3D model generation module 175 of the multidimensional tracking system 100 can combine the plurality of cross-sectional images that each define a two-dimensional cross-sectional image space $S_{CS}=<x_{CS}, y_{CS}>$ to correlate objects and structures within the cross-sectional images with the parent virtual space $S_V$, which is usually a 3-dimensional space. FIG. 13 illustrates a cross-sectional imaging "slice" 210N, which can be an MRI image slice, particularly an $N^{th}$ slice of a plurality of slices of an MRI sequence. As illustrated, the cross-sectional imaging slice 210N defines $S_{CS}=<x_{CS}, y_{CS}>$. Cross-sectional image "slices" can be "stacked" according to their respective locations that they represent in the real 3D space. An example combination of a plurality of cross-sectional imaging slices 210 is illustrated (denoted in the example as "210(N−2)" through "210(N+3)", although hundreds or thousands of slices can be included), and are organized according to their respective locations in a 3D space to form a 3D anatomical model 230, which is a 3D virtual object that can be defined with respect to the parent virtual space $S_V$. This is useful especially when designating landmark objects and regions of interest.

4. Non-Surgical Example

Figure 14:
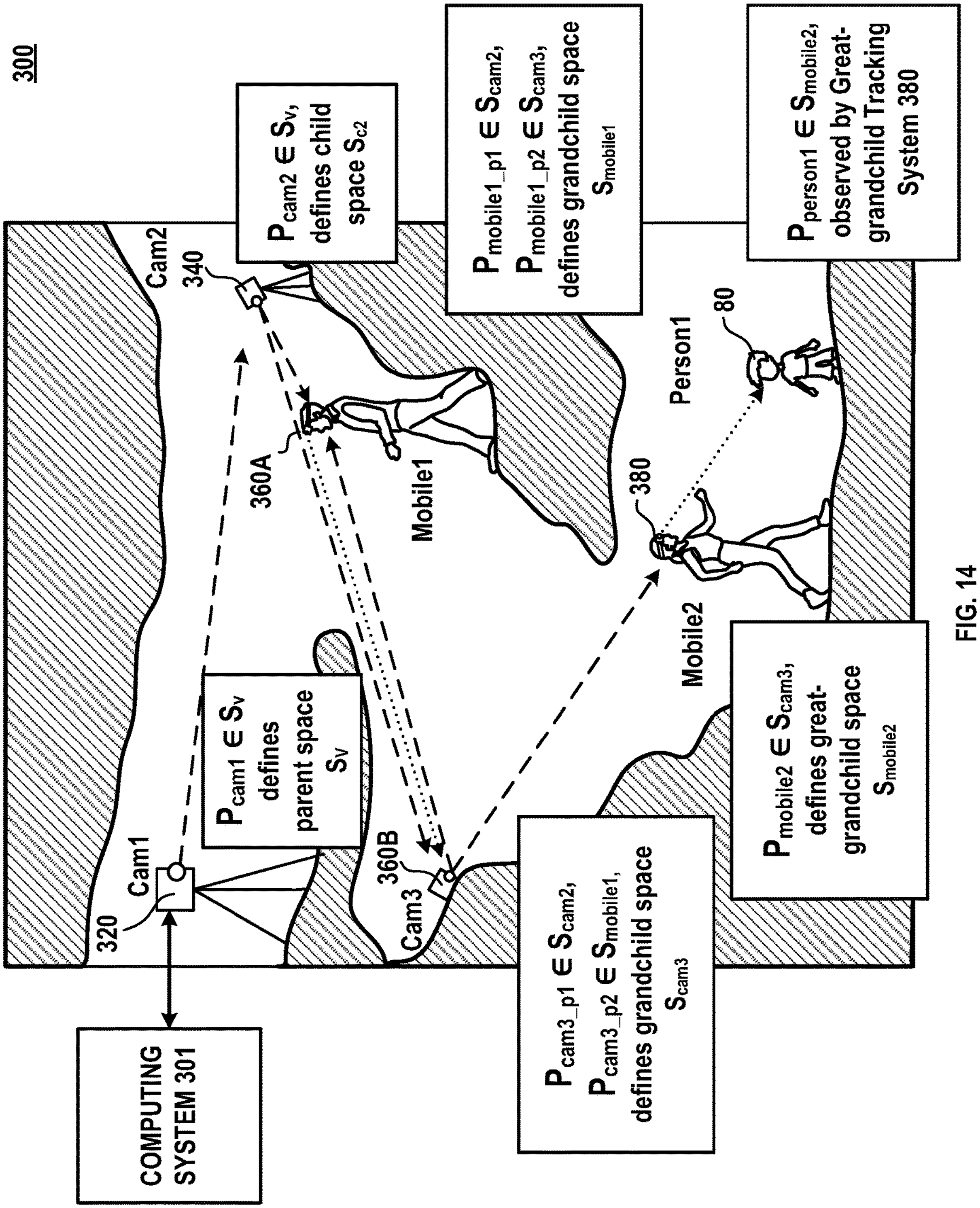
FIG. 14 is a diagram showing an example multidimensional tracking system according to the diagram of FIG. 1A in a non-surgical setting.

FIG. 14 illustrates an example embodiment of a multidimensional tracking system 300 used in a non-surgical setting. For instance, the multidimensional tracking system 300 can be used in settings where navigation throughout an unfamiliar space and object tracking are necessary, such as for a rescue or exploration mission. In the non-limiting example of FIG. 14, the multidimensional tracking system 300 is shown for tracking objects and individuals within a cave system using various image capture devices, including stationary cameras and mobile cameras. In this example, a first stationary camera Cam1 is provided that serves as a parent tracking system 320 in communication with a computing system 301, provided the first stationary camera Cam1 is operable to track positions of objects within its field-of-view. The first stationary camera Cam1 serving as the parent tracking system 320 defining the parent space $S_V$ can have a position $P_{cam1} \in S_V$. The first stationary camera Cam1 serving as the parent tracking system 320 can observe a position of a second stationary camera Cam2 which can serve as a child tracking system 340 defining a child space $S_{cam2}$ and having a position $P_{cam2} \in S_V$. The second stationary camera Cam2 serving as the child tracking system 340 can observe a position of a first mobile camera Mobile1, which can serve as a first grandchild tracking system 360A defining a first grandchild space $S_{mobile1}$ and a first position $P_{mobile1\_p1} \in S_{cam2}$. The second stationary camera Cam2 serving as the child tracking system 340 can also observe a position of a third stationary camera Cam3, which can serve as a second grandchild tracking system 360B defining a second grandchild space $S_{cam3}$ and a first position $P_{cam3\_p1} \in S_{cam2}$. Note that in this example, both the first grandchild tracking system 360A and the second grandchild tracking system 360B can observe one another; as such, the first grandchild tracking system 360A can have a second position $P_{mobile1\_p2} \in S_{cam3}$ and the second grandchild tracking system 360B can have a second position $P_{cam3\_p2} \in S_{mobile1}$. Since Mobile1 is observed by both Cam2 and Cam 3 (and is also the grandchild tracking system 360A), as a result, Mobile1 has the first position $P_{mobile1\_p1} \in S_{cam2}$ in child space $S_{cam2}$ and a second position $P_{mobile1\_p2} \in S_{cam3}$ in grandchild space $S_{cam3}$. Both positions are translatable to parent space $S_V$. Further, the second grandchild tracking system 360B observes a second mobile camera Mobile2 that serves as a great-grandchild tracking system 380 defining a great-grandchild space $S_{mobile2}$ and a first position $P_{mobile2} \in S_{cam3}$. The great-grandchild tracking system 380 can observe a non-tracking object 80 (Person1), which has a position $P_{person1}$ in great-grandchild space $S_{mobile2}$. The position $P_{person1} \in S_{mobile2}$ Of non-tracking object 80 (e.g., Person1) is translatable to parent space $S_V$ (e.g., $P_{person1} \in S_{mobile2}$; $S_{mobile2} \rightarrow S_{cam3}$; $S_{cam3} \rightarrow S_{cam2}$; $S_{cam3} \rightarrow S_{mobile1}$; $S_{mobile1} \rightarrow S_{cam2}$; $S_{cam2} \rightarrow S_V$).

It should be noted that while the non-surgical example of the multidimensional tracking system 300 is shown in the context of navigation and object tracking within a cave system, other embodiments of the multidimensional tracking system 100 are not limited to this example. Further, this example uses optical methods for positional estimation, however it should be noted that for non-surgical applications, embodiments of the multidimensional tracking system 100 can use other modalities such as electromagnetic positional estimation or sonar-based positional estimation.

5. Methods

FIGS. 15A-15E illustrate a method 400 for object tracking and spatial navigation by the multidimensional tracking system 100. Referring first to FIG. 15A, at block 402, the method includes recording, by a parent tracking system, a first virtual space position representative of an observed physical position of a first tracked object in terms of a parent virtual space representative of the physical space, wherein the parent tracking system defines a parent tracking system position within the parent virtual space. Block 404 includes recording, by a child tracking system, a second virtual space position representative of an observed physical position of the first tracked object in terms of a child virtual space representative of the physical space, wherein an observed physical position of the child tracking system is observed by the parent tracking system and defines a child tracking system position within the parent virtual space. Block 406 includes generating a first mapping between the child virtual space and the parent virtual space based on a first positional relationship between the parent tracking system position and the child tracking system position within the parent virtual space. Block 408 includes translating the second virtual space position of the first tracked object from the child virtual space to the parent virtual space based on a first mapping between the child virtual space and the parent virtual space. Block 410 includes displaying, at a display device, a first image representative of the first tracked object in terms of the parent virtual space.

Referring to FIG. 15B, further aspects of method 400 are provided. Following block 404, a subsequent block 412 includes recording, by a grandchild tracking system, a third virtual space position representative of an observed physical position of the first tracked object in terms of a grandchild virtual space representative of the physical space, wherein an observed physical position of the grandchild tracking system is observable by the child tracking system and defines a grandchild tracking system position within the child virtual space. At block 414, the method 400 includes generating a second mapping between the grandchild virtual space and the child virtual space based on a second positional relationship between the child tracking system position and the grandchild tracking system position within the child virtual space. Block 416 includes translating the third virtual space position of the first tracked object from the grandchild virtual space to the child virtual space based on the second mapping between the grandchild virtual space and the child virtual space. Block 418 includes translating the third virtual space position of the first tracked object from the child virtual space to the parent virtual space following translation of the third virtual space position from the grandchild virtual space to the child virtual space based on the first mapping between the child virtual space and the parent virtual space.

Referring to FIG. 15C, additional aspects of method 400 are illustrated. Following block 412, block 420 includes recording, by the child tracking system or the grandchild tracking system, a fourth virtual space position representative of an observed physical position of a second tracked object in terms of the child virtual space representative of the physical space or in terms of the grandchild virtual space representative of the physical space. Block 422 includes translating the fourth virtual space position of the second tracked object from the child virtual space or the grandchild virtual space to the parent virtual space based on the first mapping between the child virtual space and the parent virtual space or based on the second mapping between the grandchild virtual space and the child virtual space. Block 424 includes displaying, at the display device, a second image representative of a second tracked object in terms of the parent virtual space superimposed over the first image of the first tracked object.

FIG. 15D shows additional steps of method 400. Block 430 shows iteratively identifying, for each tracked object of one or more tracked objects, a positional error between at least two of:

- the first virtual space position of the tracked object as represented within the parent virtual space;
- the second virtual space position of the tracked object as translated from the child virtual space to the parent virtual space; and/or
- the third virtual space position of the tracked object as translated from the grandchild virtual space to the parent virtual space.

Block 432 includes updating one or more positional estimation parameters of the grandchild tracking system, the child tracking system or the parent tracking system based on the positional error. Block 434 includes updating the first mapping between the child virtual space and the parent virtual space or the second mapping between the grandchild virtual space and the child virtual space based on the positional error. Block 436 includes iteratively updating a virtual space position of the associated tracked object within an object library based on a temporal difference between the first virtual space position, the second virtual space position, or the third virtual space position of the associated tracked object taken at a first timestamp and the first virtual space position, the second virtual space position, or the third virtual space position of the associated tracked object taken at a second timestamp.

FIG. 15E further illustrates additional aspects of method 400. Block 440 shows receiving a fifth virtual space position indicative of an expected location of a landmark object relative to the parent virtual space, the child virtual space, and/or a grandchild virtual space. Block 442 includes displaying, at the display device, an identifier representative of the landmark object based on the fifth virtual space position of the landmark object with respect to the parent virtual space, the child virtual space, and/or the grandchild virtual space. Block 444 includes recording, by the parent tracking system, the child tracking system or the grandchild tracking system, a sixth virtual space position representative of an observed physical position of the landmark object with respect to the parent virtual space, the child virtual space, and/or the grandchild virtual space. Block 446 includes iteratively identifying a positional error between the fifth virtual space position of the landmark object and the sixth virtual space position of the landmark object with respect to the parent virtual space, the child virtual space or the grandchild virtual space. Block 448 describes updating, at the display device, the identifier representative of the landmark object based on the sixth virtual space position of the landmark object with respect to the parent virtual space, the child virtual space, and/or the grandchild virtual space. Block 450 provides the step of updating one or more positional estimation parameters of the grandchild tracking system, the child tracking system and/or the parent tracking system based on the positional error.

6. Computer-Implemented System

Figure 16:
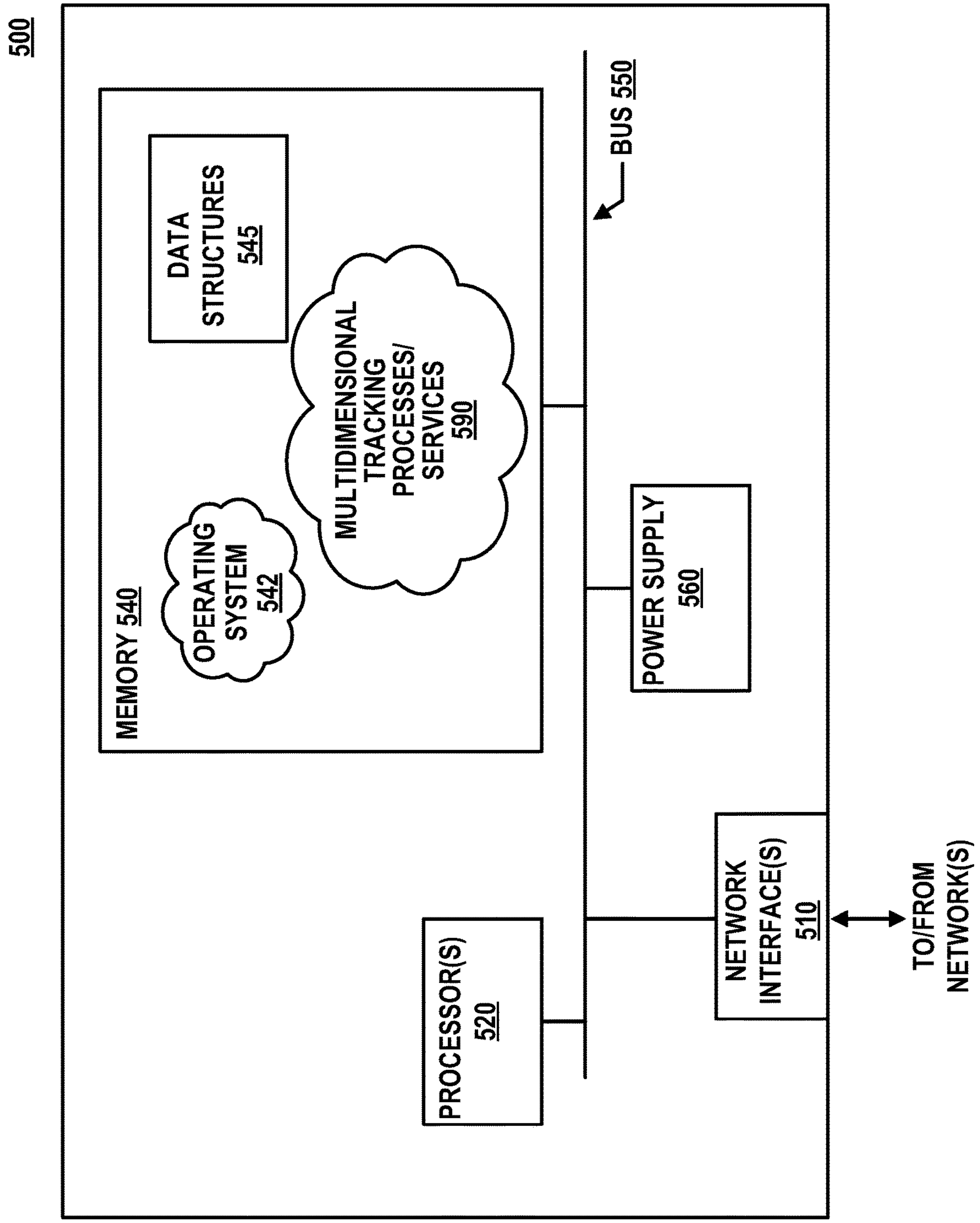
FIG. 16 is a simplified diagram showing an exemplary computing system for implementation of the system of FIG. 1A.

FIG. 16 is a schematic block diagram of an example device 500 that may be used with one or more embodiments described herein, e.g., as a component of multidimensional tracking system 100 and/or as computing system 101 shown in FIG. 1A.

Device 500 comprises one or more network interfaces 510 (e.g., wired, wireless, PLC, etc.), at least one processor 520, and a memory 540 interconnected by a system bus 550, as well as a power supply 560 (e.g., battery, plug-in, etc.).

Network interface(s) 510 include the mechanical, electrical, and signaling circuitry for communicating data over the communication links coupled to a communication network. Network interfaces 510 are configured to transmit and/or receive data using a variety of different communication protocols. As illustrated, the box representing network interfaces 510 is shown for simplicity, and it is appreciated that such interfaces may represent different types of network connections such as wireless and wired (physical) connections. Network interfaces 510 are shown separately from power supply 560, however it is appreciated that the interfaces that support PLC protocols may communicate through power supply 560 and/or may be an integral component coupled to power supply 560.

Memory 540 includes a plurality of storage locations that are addressable by processor 520 and network interfaces 510 for storing software programs and data structures associated with the embodiments described herein. In some embodiments, device 500 may have limited memory or no memory (e.g., no memory for storage other than for programs/processes operating on the device and associated caches).

Processor 520 comprises hardware elements or logic adapted to execute the software programs (e.g., instructions) and manipulate data structures 545. An operating system 542, portions of which are typically resident in memory 540 and executed by the processor, functionally organizes device 500 by, inter alia, invoking operations in support of software processes and/or services executing on the device. These software processes and/or services may include multidimensional tracking processes/services 590, which can include aspects of method 400 and/or implementations of various modules described herein including child space mapping module 130, grandchild space mapping module 150, calibration module 111, correction module 115, 3D model generation module 175, and/or combination module 170. Note that while multidimensional tracking processes/services 590 is illustrated in centralized memory 540, alternative embodiments provide for the process to be operated within the network interfaces 510, such as a component of a MAC layer, and/or as part of a distributed computing network environment.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules or engines configured to operate in accordance with the techniques herein (e.g., according to the functionality of a similar process). In this context, the term module and engine may be interchangeable. In general, the term module or engine refers to model or an organization of interrelated software components/functions. Further, while the multidimensional tracking processes/services 590 is shown as a standalone process, those skilled in the art will appreciate that this process may be executed as a routine or module within other processes.

7. Machine Learning Models

Figure 17:
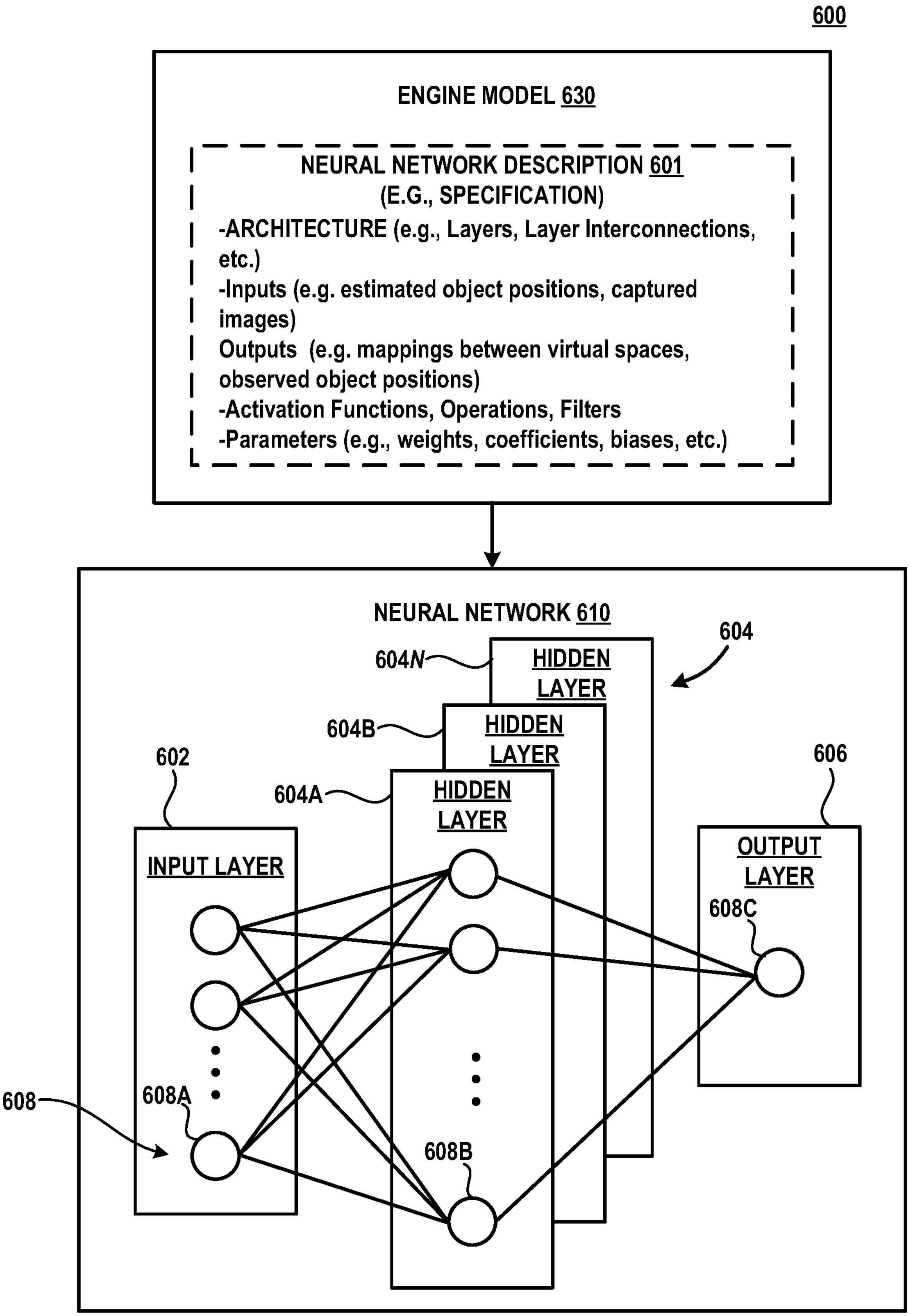
FIG. 17 is a simplified diagram showing an example neural network architecture model for implementation of aspects of the multidimensional tracking system of FIG. 1A.

FIG. 17 is a schematic block diagram of an example neural network architecture 600 that may be used with one or more embodiments described herein, e.g., as a component of multidimensional tracking system 100 shown in FIG. 1A, and particularly as a component of the one or more child mapping machine learning models 136 (FIG. 6) and the one or more grandchild mapping machine learning models 156 (FIG. 8) and/or as a component of one or more of the hierarchical tracking sub-systems 110 (i.e. employed by the parent tracking system 120, the child tracking system(s), 140 and/or the grandchild tracking system(s) 160 for positional estimation). Other possible implementations of the neural network architecture 600 can be used by the multidimensional tracking system 100 to identify landmark objects present within imaging captured by the hierarchical tracking sub-systems 110. In some embodiments, the neural network architecture 600 can be used by the multidimensional tracking system 100 to predict anatomical shift given repeated or iterative observation of deformations and anatomical shift across a plurality of datasets that are either region specific or globally applicable for the subject anatomical structure.

Architecture 600 includes a neural network 610 defined by an example neural network description 601 in an engine model (neural controller) 630. The neural network 610 can represent a neural network implementation of a child space mapping engine, grandchild space mapping engine, and/or positional estimation engine(s) for one or more of the hierarchical tracking sub-systems 110. The neural network description 601 can include a full specification of the neural network 610, including the neural network architecture 600. For example, the neural network description 601 can include a description or specification of the architecture 600 of the neural network 610 (e.g., the layers, layer interconnections, number of nodes in each layer, etc.); an input and output description which indicates how the input and output are formed or processed; an indication of the activation functions in the neural network, the operations or filters in the neural network, etc.; neural network parameters such as weights, biases, etc.; and so forth.

The neural network 610 reflects the architecture 600 defined in the neural network description 601. In an example corresponding to child mapping machine learning model(s) 136, the neural network 610 includes an input layer 602, which includes input data, such as a set of observed positions and/or orientations of tracked objects that are common between the parent tracking system 120 and the child tracking system(s) 140, with an individual observed position of one such tracked object corresponding to one or more nodes 608. In one illustrative example, the input layer 602 can include data representing a portion of input media data such as a patch of data or pixels (e.g., a 128×128 patch of data) in an image captured by the parent tracking system 120 and/or the child tracking system(s) 140 that includes one or more tracked objects and can include a listing of one or more observed object position values. Similar logic can be applied with respect to grandchild mapping machine learning model(s) 156.

The neural network 610 includes hidden layers 604A through 604N (collectively "604" hereinafter). The hidden layers 604 can include n number of hidden layers, where n is an integer greater than or equal to one. The number of hidden layers can include as many layers as needed for a desired processing outcome and/or rendering intent. The neural network 610 further includes an output layer 606 that provides an output (e.g., a mapping that translates a child virtual space to a parent virtual space) resulting from the processing performed by the hidden layers 604. In an illustrative example corresponding to the child mapping machine learning model(s) 136, the output layer 606 can provide a mapping between the parent space $S_V$ defined by the parent tracking system 120 and the child space $S_{CHILD}$ defined by the child tracking system(s) 140 based on the images and/or observed object position values provided to the input layer 602.

The neural network 610 in this example is a multi-layer neural network of interconnected nodes. Each node can represent a piece of information. Information associated with the nodes is shared among the different layers and each layer retains information as information is processed. In some cases, the neural network 610 can include a feed-forward neural network, in which case there are no feedback connections where outputs of the neural network are fed back into itself. In other cases, the neural network 610 can include a recurrent neural network, which can have loops that allow information to be carried across nodes while reading in input.

Information can be exchanged between nodes through node-to-node interconnections between the various layers. Nodes of the input layer 602 can activate a set of nodes in the first hidden layer 604A. For example, as shown, each of the input nodes of the input layer 602 is connected to each of the nodes of the first hidden layer 604A. The nodes of the hidden layer 604A can transform the information of each input node by applying activation functions to the information. The information derived from the transformation can then be passed to and can activate the nodes of the next hidden layer (e.g., 604B), which can perform their own designated functions. Example functions include convolutional, up-sampling, data transformation, pooling, and/or any other suitable functions. The output of the hidden layer (e.g., 604B) can then activate nodes of the next hidden layer (e.g., 604N), and so on. The output of the last hidden layer can activate one or more nodes of the output layer 606, at which point an output is provided. In some cases, while nodes (e.g., nodes 608A, 608B, 608C) in the neural network 610 are shown as having multiple output lines, a node has a single output and all lines shown as being output from a node represent the same output value.

In some cases, each node or interconnection between nodes can have a weight that is a set of parameters derived from training the neural network 610. For example, an interconnection between nodes can represent a piece of information learned about the interconnected nodes. The interconnection can have a numeric weight that can be tuned (e.g., based on a training dataset), allowing the neural network 610 to be adaptive to inputs and able to learn as more data is processed.

The neural network 610 can be pre-trained to process the features from the data in the input layer 602 using the different hidden layers 604 in order to provide the output through the output layer 606. In an example the child mapping machine learning model(s) 136, in which the neural network 610 is used to learn mappings between the parent virtual space $S_V$ and one or more child virtual spaces $S_{CHILD}$, the neural network 610 can be trained using training data that includes example mappings from a training dataset. For instance, training data can be input into the neural network 610, which can be processed by the neural network 610 to generate outputs which can be used to tune one or more aspects of the neural network 610, such as weights, biases, etc.

In some cases, the neural network 610 can adjust weights of nodes using a training process called backpropagation. Backpropagation can include a forward pass, a loss function, a backward pass, and a weight update. The forward pass, loss function, backward pass, and parameter update is performed for one training iteration. The process can be repeated for a certain number of iterations for each set of training media data until the weights of the layers are accurately tuned.

For a first training iteration for the neural network 610, the output can include values that do not give preference to any particular class due to the weights being randomly selected at initialization. For example, if the output is a vector with probabilities that the object includes different product(s) and/or different users, the probability value for each of the different product and/or user may be equal or at least very similar (e.g., for ten possible products or users, each class may have a probability value of 0.1). With the initial weights, the neural network 610 is unable to determine low level features and thus cannot make an accurate determination of what the classification of the object might be. A loss function can be used to analyze errors in the output. Any suitable loss function definition can be used.

The loss (or error) can be high for the first training dataset (e.g., images) since the actual values will be different than the predicted output. The goal of training is to minimize the amount of loss so that the predicted output comports with a target or ideal output. The neural network 610 can perform a backward pass by determining which inputs (weights) most contributed to the loss of the neural network 610, and can adjust the weights so that the loss decreases and is eventually minimized.

A derivative of the loss with respect to the weights can be computed to determine the weights that contributed most to the loss of the neural network 610. After the derivative is computed, a weight update can be performed by updating the weights of the filters. For example, the weights can be updated so that they change in the opposite direction of the gradient. A learning rate can be set to any suitable value, with a high learning rate including larger weight updates and a lower value indicating smaller weight updates.

The neural network 610 can include any suitable neural or deep learning network. One example includes a convolutional neural network (CNN), which includes an input layer and an output layer, with multiple hidden layers between the input and out layers. The hidden layers of a CNN include a series of convolutional, nonlinear, pooling (for downsampling), and fully connected layers. In other examples, the neural network 610 can represent any other neural or deep learning network, such as an autoencoder, a deep belief nets (DBNs), and recurrent neural networks (RNNs), etc.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The invention claimed is:

1. A system, comprising:

a parent tracking system that defines a parent virtual space representative of a physical space, wherein the parent tracking system defines a parent tracking system position within the parent virtual space, and wherein the parent tracking system is operable to record a first virtual space position representative of an observed physical position of a first tracked object in the physical space in terms of the parent virtual space;

a child tracking system that defines a child virtual space representative of the physical space, wherein an observed physical position of the child tracking system is observed by the parent tracking system and defines a child tracking system position within the parent virtual space, wherein the child tracking system is operable to record a second virtual space position representative of an observed physical position of the first tracked object in the physical space in terms of the child virtual space; and a processor in communication with a memory, the parent tracking system, and the child tracking system, the memory including instructions encoded thereon, which, when executed, cause the processor to:

(a) generate a first mapping between the child virtual space and the parent virtual space based on a first positional relationship between the parent tracking system position and the child tracking system position within the parent virtual space;

(b) translate the child virtual space to the parent virtual space based on the first mapping between the child virtual space and the parent virtual space;

(c) iteratively identify a positional error between the first virtual space position of the first tracked object as represented within the parent virtual space and the second virtual space position of the first tracked object as translated from the child virtual space to the parent virtual space; and (d) update the first mapping between the child virtual space and the parent virtual space based on the positional error.

2. The system of claim 1, wherein the memory includes instructions, which, when executed, further cause the processor to:

update one or more positional estimation parameters of the child tracking system or the parent tracking system based on the positional error.

3. The system of claim 1, wherein the memory includes instructions, which, when executed, further cause the processor to:

iteratively update a virtual space position of the first tracked object within an object library based on a temporal difference between the first virtual space position or the second virtual space position of the first tracked object taken at a first timestamp and the first virtual space position or the second virtual space position of the first tracked object taken at a second timestamp.

4. The system of claim 1, further comprising:

a grandchild tracking system in communication with the processor, the grandchild tracking system defining a grandchild virtual space representative of the physical space, wherein an observed physical position of the grandchild tracking system is observable by the child tracking system and defines a grandchild tracking system position within the child virtual space.

5. The system of claim 4, wherein the grandchild tracking system is operable to record a third virtual space position representative of an observed physical position of a first tracked object in terms of the grandchild virtual space.

6. The system of claim 5, wherein the memory includes instructions, which, when executed, further cause the processor to:

translate the third virtual space position of the first tracked object from the grandchild virtual space to the child virtual space based on a second mapping between the grandchild virtual space and the child virtual space.

7. The system of claim 6, wherein the memory includes instructions, which, when executed, further cause the processor to:

generate the second mapping between the grandchild virtual space and the child virtual space based on a second positional relationship between the grandchild tracking system position within the child virtual space and the child tracking system position.

8. The system of claim 6, wherein the memory includes instructions, which, when executed, further cause the processor to:

translate the third virtual space position of the first tracked object from the child virtual space to the parent virtual space based on the first mapping between the child virtual space and the parent virtual space.

9. The system of claim 8, wherein the memory includes instructions, which, when executed, further cause the processor to:

iteratively identify a positional error between at least two of:

a first virtual space position of the first tracked object as represented within the parent virtual space;

a second virtual space position of the first tracked object as translated from the child virtual space to the parent virtual space; and/or the third virtual space position of the first tracked object as translated from the grandchild virtual space to the parent virtual space.

10. The system of claim 9, wherein the memory includes instructions, which, when executed, further cause the processor to:

update one or more positional estimation parameters of the grandchild tracking system, the child tracking system or the parent tracking system based on the positional error; and/or update the first mapping between the child virtual space and the parent virtual space or the second mapping between the grandchild virtual space and the child virtual space based on the positional error.

11. The system of claim 9, wherein the memory includes instructions, which, when executed, further cause the processor to:

iteratively update a virtual space position of the first tracked object within an object library based on a temporal difference between the first virtual space position, the second virtual space position, or the third virtual space position of the first tracked object taken at a first timestamp and the first virtual space position, the second virtual space position, or the third virtual space position of the first tracked object taken at a second timestamp.

12. The system of claim 1, wherein the memory includes instructions, which, when executed, further cause the processor to:

display, at a display device in communication with the processor, a first image representative of the first tracked object in terms of the parent virtual space.

13. The system of claim 12, wherein the memory includes instructions, which, when executed, further cause the processor to:

display, at the display device, a second image representative of a second tracked object in terms of the parent virtual space superimposed over the first image of the first tracked object.

14. The system of claim 1, wherein the child tracking system is operable to record a fourth virtual space position representative of an observed physical position of a second tracked object in the physical space in terms of the child virtual space representative of the physical space.

15. The system of claim 14, wherein the memory includes instructions, which, when executed, further cause the processor to:

translate the fourth virtual space position of the second tracked object from the child virtual space to the parent virtual space based on the first mapping between the child virtual space and the parent virtual space.

16. The system of claim 1, wherein the parent tracking system and the child tracking system are operable to record the first virtual space position and the second virtual space position by at least one of:

one or more image capture devices of the parent tracking system or the child tracking system that capture a plurality of captured images that include the first tracked object;

one or more electromagnetic position estimation devices of the parent tracking system or the child tracking system that capture electromagnetic data indicative of an estimated position of the first tracked object; and/or one or more sonic position estimation devices of the parent tracking system or the child tracking system that capture sonic data indicative of the first virtual space position of the first tracked object or the second virtual space position of the first tracked object.

17. The system of claim 16, wherein the parent tracking system and the child tracking system are operable to:

estimate the first virtual space position of the first tracked object or the second virtual space position of the first tracked object with respect to the parent virtual space or the child virtual space using the plurality of captured images, the electromagnetic data, and/or the sonic data through application of a computer-vision technique.

18. The system of claim 1, wherein the memory includes instructions, which, when executed, further cause the processor to:

receive, at the processor, a fifth virtual space position representative of an expected location of a landmark object relative to the parent virtual space, the child virtual space, and/or a grandchild virtual space; and display, at a display device in communication with the processor, an identifier representative of the landmark object based on the fifth virtual space position of the landmark object with respect to the parent virtual space, the child virtual space, and/or the grandchild virtual space.

19. The system of claim 18, wherein the memory includes instructions, which, when executed, further cause the processor to:

record, by the parent tracking system, the child tracking system or a grandchild tracking system in communication with the processor, a sixth virtual space position representative of an observed physical position of the landmark object with respect to the parent virtual space, the child virtual space, and/or the grandchild virtual space;

iteratively identify, by the processor, a positional error between the fifth virtual space position of the landmark object and the sixth virtual space position of the landmark object with respect to the parent virtual space, the child virtual space or the grandchild virtual space; and update, at the display device, the identifier representative of the landmark object based on the sixth virtual space position of the landmark object with respect to the parent virtual space, the child virtual space, and/or the grandchild virtual space.

20. The system of claim 19, wherein the memory includes instructions, which, when executed, further cause the processor to:

update one or more positional estimation parameters of the grandchild tracking system, the child tracking system and/or the parent tracking system based on the positional error.

21. The system of claim 1, wherein the parent tracking system is a stereotactic navigation system.

22. The system of claim 1, wherein the child tracking system is an operating microscope.

23. A system, comprising:

a parent tracking system operable to record a first virtual space position representative of an observed physical position of a first tracked object in a physical space in terms of a parent virtual space representative of the physical space, wherein the parent tracking system defines a parent tracking system position within the parent virtual space;

a child tracking system operable to record a second virtual space position representative of an observed physical position of the first tracked object in the physical space in terms of a child virtual space representative of the physical space, and further operable to record a fourth virtual space position representative of an observed physical position of a second tracked object in the physical space in terms of the child virtual space representative of the physical space, wherein an observed physical position of the child tracking system is observable by the parent tracking system and defines a child tracking system position within the parent virtual space; and a processor in communication with a memory, the parent tracking system, and the child tracking system, the memory including instructions encoded thereon, which, when executed, cause the processor to;

(a) generate a first mapping between the child virtual space and the parent virtual space based on a first positional relationship between the parent tracking system position and the child tracking system position within the parent virtual space;

(b) translate the fourth virtual space position representative of the second tracked object from the child virtual space to the parent virtual space based on the first mapping between the child virtual space and the parent virtual space;

(c) iteratively identify a positional error between the first virtual space position of the first tracked object as represented within the parent virtual space and the second virtual space position of the first tracked object as translated from the child virtual space to the parent virtual space; and (d) update the first mapping between the child virtual space and the parent virtual space based on the positional error.

24. The system of claim 23, wherein the memory includes instructions, which, when executed, further cause the processor to:

display, at a display device in communication with the processor, a first image representative of the first tracked object in terms of the parent virtual space; and display, at the display device, a second image representative of the second tracked object in terms of the parent virtual space superimposed over the first image of the first tracked object.

25. The system of claim 23, further comprising:

a grandchild tracking system in communication with the processor, the grandchild tracking system being operable to record a seventh virtual space position representative of an observed physical position of a third tracked object in the physical space in terms of a grandchild virtual space representative of the physical space, wherein an observed physical position of the grandchild tracking system is observable by the child tracking system and defines a grandchild tracking system position within the child virtual space.

26. The system of claim 25, wherein the memory includes instructions, which, when executed, further cause the processor to:

translate the seventh virtual space position of the third tracked object from the grandchild virtual space to the child virtual space based on a second mapping between the grandchild virtual space and the child virtual space.

27. The system of claim 26, wherein the memory includes instructions, which, when executed, further cause the processor to:

generate the second mapping between the grandchild virtual space and the child virtual space based on a second positional relationship between the grandchild tracking system position and the child tracking system position within the child virtual space.

28. The system of claim 26, wherein the memory includes instructions, which, when executed, further cause the processor to:

translate the seventh virtual space position of the third tracked object from the child virtual space to the parent virtual space based on the first mapping between the child virtual space and the parent virtual space.

29. The system of claim 28, wherein the memory includes instructions, which, when executed, further cause the processor to:

display, at a display device in communication with the processor, a third image of the third tracked object in terms of the parent virtual space superimposed over an image representative of the first tracked object in terms of the parent virtual space.

30. A method, comprising:

recording, by a parent tracking system, a first virtual space position representative of an observed physical position of a first tracked object in a physical space in terms of a parent virtual space representative of the physical space, wherein the parent tracking system defines a parent tracking system position within the parent virtual space;

recording, by a child tracking system, a second virtual space position representative of an observed physical position of the first tracked object in the physical space in terms of a child virtual space representative of the physical space, wherein an observed physical position of the child tracking system is observed by the parent tracking system and defines a child tracking system position within the parent virtual space;

generating, by a processor in communication with a memory, a first mapping between the child virtual space and the parent virtual space based on a first positional relationship between the parent tracking system position and the child tracking system position within the parent virtual space, the processor being in communication with the parent tracking system and the child tracking system;

translating, by the processor, the second virtual space position of the first tracked object from the child virtual space to the parent virtual space based on the first mapping between the child virtual space and the parent virtual space;

iteratively identifying, by the processor, a positional error between the first virtual space position of the first tracked object as represented within the parent virtual space and the second virtual space position of the first tracked object as translated from the child virtual space to the parent virtual space; and updating, by the processor, the first mapping between the child virtual space and the parent virtual space based on the positional error.

31. The method of claim 30, further comprising:

updating, by the processor, one or more positional estimation parameters of the child tracking system or the parent tracking system based on the positional error.

32. The method of claim 30, further comprising:

iteratively updating a virtual space position of the first tracked object within an object library based on a temporal difference between the first virtual space position or the second virtual space position of the first tracked object taken at a first timestamp and the first virtual space position or the second virtual space position of the first tracked object taken at a second timestamp.

33. The method of claim 30, further comprising:

recording, by a grandchild tracking system in communication with the processor, a third virtual space position representative of an observed physical position of the first tracked object in the physical space in terms of a grandchild virtual space representative of the physical space, wherein an observed physical position of the grandchild tracking system is observable by the child tracking system and defines a grandchild tracking system position within the child virtual space.

34. The method of claim 33, further comprising:

translating, by the processor, the third virtual space position of the first tracked object from the grandchild virtual space to the child virtual space based on a second mapping between the grandchild virtual space and the child virtual space.

35. The method of claim 34, further comprising:

generating, by the processor, the second mapping between the grandchild virtual space and the child virtual space based on a second positional relationship between the grandchild tracking system position within the child virtual space and the child tracking system position.

36. The method of claim 34, further comprising:

translating, by the processor, the third virtual space position of the first tracked object from the child virtual space to the parent virtual space based on the first mapping between the child virtual space and the parent virtual space.

37. The method of claim 36, further comprising:

iteratively identifying, by the processor, a positional error between at least two of:

the first virtual space position of the first tracked object as represented within the parent virtual space;

the second virtual space position of the first tracked object as translated from the child virtual space to the parent virtual space; and/or the third virtual space position of the first tracked object as translated from the grandchild virtual space to the parent virtual space.

38. The method of claim 37, further comprising:

updating, by the processor, one or more positional estimation parameters of the grandchild tracking system, the child tracking system or the parent tracking system based on the positional error; and/or updating, by the processor, the first mapping between the child virtual space and the parent virtual space or the second mapping between the grandchild virtual space and the child virtual space based on the positional error.

39. The method of claim 36, further comprising:

iteratively updating a virtual space position of the first tracked object within an object library based on a temporal difference between the first virtual space position, the second virtual space position, or the third virtual space position of the first tracked object taken at a first timestamp and the first virtual space position, the second virtual space position, or the third virtual space position of the first tracked object taken at a second timestamp.

40. The method of claim 30, further comprising:

displaying, at a display device in communication with the processor, a first image representative of the first tracked object in terms of the parent virtual space.

41. The method of claim 40, further comprising:

displaying, at the display device, a second image representative of a second tracked object in terms of the parent virtual space superimposed over the first image of the first tracked object.

42. The method of claim 30, further comprising:

recording, by the child tracking system, a fourth virtual space position representative of an observed physical position of a second tracked object in the physical space in terms of the child virtual space representative of the physical space.

43. The method of claim 42, further comprising:

translating, by the processor, the fourth virtual space position of the second tracked object from the child virtual space to the parent virtual space based on the first mapping between the child virtual space and the parent virtual space.

44. The method of claim 30, further comprising:

receiving, at the processor, a fifth virtual space position indicative of an expected location of a landmark object relative to the parent virtual space, the child virtual space, and/or a grandchild virtual space; and displaying, at a display device in communication with the processor, an identifier representative of the landmark object based on the fifth virtual space position of the landmark object with respect to the parent virtual space, the child virtual space, and/or the grandchild virtual space.

45. The method of claim 44, further comprising:

recording, by the parent tracking system, the child tracking system or a grandchild tracking system in communication with the processor, a sixth virtual space position representative of an observed physical position of the landmark object with respect to the parent virtual space, the child virtual space, and/or the grandchild virtual space;

iteratively identifying, by the processor, a positional error between the fifth virtual space position of the landmark object and the sixth virtual space position of the landmark object with respect to the parent virtual space, the child virtual space or the grandchild virtual space; and updating, at the display device, the identifier representative of the landmark object based on the sixth virtual space position of the landmark object with respect to the parent virtual space, the child virtual space, and/or the grandchild virtual space.

46. The method of claim 45, further comprising:

updating one or more positional estimation parameters of the grandchild tracking system, the child tracking system and/or the parent tracking system based on the positional error.

* * * * *